(12) United States Patent
Collins et al.

(10) Patent No.: US 9,804,062 B2
(45) Date of Patent: Oct. 31, 2017

(54) APPARATUS AND METHOD FOR TESTING MULTIPLE SAMPLES

(71) Applicant: BP EXPLORATION OPERATING COMPANY LIMITED, Middlesex (GB)

(72) Inventors: Ian Ralph Collins, Middlesex (GB); John William Couves, Middlesex (GB); Bogdan Costin Gagea, Berkshire (GB); Arnaud Lager, Middlesex (GB); Kevin John Webb, Middlesex (GB)

(73) Assignee: BP Exploration Operating Company Limited

( * ) Notice: Subject to any disclaimer, the term of this patent is extended or adjusted under 35 U.S.C. 154(b) by 28 days.

(21) Appl. No.: 14/977,997

(22) Filed: Dec. 22, 2015

(65) Prior Publication Data

US 2016/0109334 A1    Apr. 21, 2016

Related U.S. Application Data

(63) Continuation of application No. 13/812,292, filed as application No. PCT/GB2011/001153 on Jul. 29, 2011, now Pat. No. 9,261,435.

(30) Foreign Application Priority Data

Aug. 6, 2010    (EP) .................................... 10251410

(51) Int. Cl.
    *E21B 43/20*     (2006.01)
    *G01N 1/00*     (2006.01)
    *G01N 15/08*     (2006.01)

(52) U.S. Cl.
    CPC ............... *G01N 1/00* (2013.01); *E21B 43/20* (2013.01); *G01N 15/082* (2013.01)

(58) Field of Classification Search
None
See application file for complete search history.

(56) References Cited

U.S. PATENT DOCUMENTS

| | | | |
|---|---|---|---|
| 3,362,473 A | 1/1968 | Foster | |
| 3,428,127 A | 2/1969 | Atkins, Jr. | |
| (Continued) | | | |

FOREIGN PATENT DOCUMENTS

| | | |
|---|---|---|
| CN | 1214757 A | 4/1999 |
| RU | 2178515 C1 | 1/2002 |
| WO | 2005/014164 A1 | 2/2005 |

OTHER PUBLICATIONS

Eurasian Search Report dated Nov. 22, 2016, for Eurasian Application No. 201600496 (2 p.).

(Continued)

*Primary Examiner* — Andre Allen
(74) *Attorney, Agent, or Firm* — John L. Wood

(57) ABSTRACT

The invention relates to an apparatus for simultaneously injecting fluids into a plurality of samples of porous media, comprising: a plurality of holders for the samples of porous media, each holder comprising a sleeve and first and second platens, the first platen having an inlet for an injection fluid and the second platen having an outlet for a produced fluid, and the samples of porous media being arranged, in use, in each of the holders such that the first platen and second platen of each holder contact a first and second end of the sample of porous medium respectively, the inlet of each first platen being in fluid communication with an injection line for injecting fluid into the sample of porous medium arranged in the holder, the outlet of each second platen being in fluid communication with a dedicated effluent line for removing fluid produced from the sample of porous medium arranged in the holder, on-line and/or off-line analytical means for analyzing the fluids injected into each of the (Continued)

samples of porous media, on-line and/or off-line means for analyzing the fluids removed from each of the samples of porous media. A method of simultaneously injecting injection fluid into the samples of porous media is also provided.

10 Claims, 7 Drawing Sheets

(56) References Cited

U.S. PATENT DOCUMENTS

| | | |
|---|---|---|
| 4,586,376 A | 5/1986 | Outmans |
| 4,597,442 A | 7/1986 | Dilgren et al. ............ 166/272.3 |
| 4,893,939 A | 1/1990 | Burk et al. |
| 5,042,580 A | 8/1991 | Cullick et al. |
| 5,060,727 A | 10/1991 | Schramm et al. ............ 166/268 |
| 5,161,407 A | 11/1992 | Ankeny et al. |
| 5,493,226 A | 2/1996 | Honarpour et al. |
| 5,767,399 A | 6/1998 | Smith et al. |
| 2005/0178189 A1 | 8/2005 | Lenormand et al. |
| 2006/0175061 A1 | 8/2006 | Crichlow ...................... 166/302 |
| 2007/0284107 A1 | 12/2007 | Crichlow ...................... 166/302 |
| 2008/0216559 A1 | 9/2008 | Hilab |
| 2009/0200084 A1 | 8/2009 | Vuyk et al. ...................... 175/67 |
| 2011/0067856 A1 | 3/2011 | Kohr ............................. 166/246 |
| 2012/0292022 A1 | 11/2012 | Choban et al. ................ 166/246 |
| 2013/0091941 A1 | 4/2013 | Huh et al. .................. 73/152.08 |
| 2013/0240205 A1 | 9/2013 | Tosi ......................... 166/250.17 |
| 2014/0131279 A1 | 5/2014 | Seibert et al. ................. 210/636 |

OTHER PUBLICATIONS

Patent Examination Report No. 1 dated Nov. 20, 2014, issued in Australian Patent Application No. 2011287419, filed Apr. 2, 2013 (6 pgs).

Office Action issued in corresponding Mexican Patent Application No. MX/a/2013/001453, dated Sep. 10, 2014 (3 pages).

Office Action issued in corresponding Eurasian Patent Application No. 201300212 (2 pages), w/English Translation dated Jan. 27, 2015 (2 pages).

Chinese First Office Action dated Apr. 1, 2015, issued in Application No. 201180048259.8, filed Jul. 29, 2011 (6 pgs.) w/English Translation (10 pgs.).

APPARATUS AND METHOD FOR TESTING MULTIPLE SAMPLES

This application is a continuation of application Ser. No. 13/812,292 filed Jan. 25, 2013 which is a 371 of PCT/GB2011/001153 filed Jul. 29, 2011, which claims priority to European Patent Application No. 10251410.6 filed Aug. 6, 2010, the entire contents of each of which are hereby incorporated by reference.

This invention relates to a method and apparatus for performing testing of waterflooding and enhanced oil recovery techniques on multiple samples of porous media.

It has long been known that only a portion of the total crude oil present in a reservoir can be recovered during a primary recovery process, this primary process resulting in oil being recovered under the natural energy of the reservoir. The reservoir typically takes the form of an oil-bearing subterranean rock formation having sufficient porosity and permeability to store and transmit fluids, and with which oil is associated, for example being held in pores or between grains of the rock formation. So-called secondary recovery techniques are used to force additional oil out of the reservoir, the simplest method of which is by direct replacement with another medium in the form of a displacement fluid (also referred to an injection fluid), usually water or gas. Enhanced oil recovery (EOR) techniques can also be used. The purpose of such EOR techniques is not only to restore or maintain reservoir pressure, but also to improve oil displacement in the reservoir, thereby minimising the residual oil saturation of the reservoir, that is, the volume of oil present in the reservoir. Where the initial reservoir pressure is close to the bubble point of the crude oil, secondary or enhanced oil recovery techniques may be used early in the life of a field, for example, primary recovery may not occur.

"Waterflooding" is one of the most successful and extensively used secondary recovery methods. Water is injected, under pressure, into reservoir rock formations via injection wells. The injected water acts to help maintain reservoir pressure, and sweeps the displaced oil ahead of it through the rock towards production wells from which the oil is recovered. The water used in waterflooding is generally saline water from a natural source such as seawater or may be a produced water (i.e. water that is separated from the crude oil at a production facility). However, it is known that the use of a lower salinity injection water (for example, brackish water such as estuarine water, or fresh water such as river water, or lake water) during water-flooding can increase the amount of oil recovered compared to the use of a higher salinity water (for example, sea water, produced water or aquifer water). It is also known that reducing the multivalent cation content of a lower salinity injection water can have an impact on the oil recovery. However, lower salinity waters, such as fresh water, are often not available at a well site, for example at offshore oilfields, and have to be made by reducing the total dissolved salt (TDS) concentration and/or the concentration of multivalent cations of a source water using desalination techniques such as reverse osmosis or forward osmosis. Source waters that are known to be treated in this manner include seawater, brackish water, produced water and aquifer water.

"Low" salinity waters for use as injection water typically have a total dissolved solids content (TDS) in the range of 200 to 15,000 ppmv, preferably, 500 to 12,000 ppmv. Where the formation rock contains swelling clays, in particular, smectite clays, a relatively high TDS for the low salinity water is required in order to stabilise the clays, thereby avoiding the risk of formation damage. Thus, where the formation rock contains an amount of swelling clays sufficient to result in formation damage, the low salinity water preferably has a total dissolved solids content (TDS) in the range of 8,000 to 15,000 ppmv, in particular, 8,000 to 12,000 ppmv. Where the formation comprises amounts of swelling clays that do not result in formation damage, the TDS of the source water is typically in the range of 200 to 8,000 ppmv, preferably 500 to 8,000 ppmv, for example, 1,000 to 5,000 ppmv. As discussed above, the low salinity water also has a low concentration of multivalent cations of typically 40 ppmv or less, preferably less than 35 ppmv, more preferably, less than 30 ppmv, for example, less than 25 ppmv. However, it is preferred that the low salinity water contains at least some multivalent cations. Thus, a multivalent cation content of the low salinity water in the range of 5 to 40 ppmv, preferably, 10 to 40 ppmv is acceptable.

The water present in the pore space of a rock, hereinafter referred to as "formation water", can vary in composition. Where a displacement fluid is injected without performing primary recovery or immediately after primary recovery, the formation water will typically comprise connate water, and where a displacement fluid is injected after a previous waterflood, the formation water will typically comprise a mixture of connate water and a previously injected water such as sea water or produced water.

The factors that control the interactions between crude oil, the rock formation, the injection or displacement fluid and the formation water, and their effect on wettability and oil recovery, involve complex and sometimes competing mechanisms.

Currently, laboratory core flood testing (where a sample of rock is removed from a reservoir and is then placed under the reservoir conditions for testing in the laboratory) or single well chemical tracer testing (where a fluid labelled with appropriate chemical tracers is injected into a formation via an injection well and is produced back from the same well) are applied in order to determine the residual oil saturation of the formation following an enhanced oil recovery technique such as a low salinity waterflood, and based on the results, a decision can be made as to whether or not an enhanced oil recovery technique such as a waterflood using a low salinity water is worthwhile. These tests are time consuming and the results are often not available during the planning stage of an oil field development meaning that equipment required for treating the injection water may not have been included in the production facility. Also, the time consuming nature of these tests means that the composition of the injection water is often not optimal for the reservoir i.e. has not been optimized for the characteristics of the reservoir rock, formation water and crude oil.

US2007/0009384 relates to an apparatus for high throughput testing of potential catalysts, which is suitable for testing a large number of catalysts by the use of a plurality of analysis methods, preferably in parallel or in quick succession. This apparatus has a reactor element which includes at least one gas inlet unit, a plurality of reaction chambers and at least one restriction unit. The restriction unit has a plurality of channels which are arranged in such a manner that at least one reaction chamber is in direct contact with at least one channel of the restriction unit. The advantage of this apparatus is that it allows for rapid screening of potential catalysts.

Conventional coreflood experiments are performed using a single sample of reservoir rock contained within a core holder. It would be advantageous to design a high throughput coreflood apparatus that would be capable of simultaneously flooding a plurality of coreflood samples under different conditions. However, the high throughput apparatus described above would be unsuitable for this purpose owing to the need for liquid inlets and outlets.

The determination of the residual oil saturation of core samples taken from an oil bearing formation following enhanced oil recovery techniques such as waterflooding in secondary or tertiary mode is time consuming owing to the length of time taken to bring a core sample to reservoir conditions prior to coreflooding (for example, waterflooding). This means that a traditional coreflood test rig takes in excess of six weeks to perform a single coreflood experiment. As understanding of the factors that result in enhanced oil recovery increases, there is a need to perform a plurality of coreflood experiments simultaneously, both to develop an understanding of the mechanisms behind enhanced oil recovery and to optimize the injection fluids (e.g. injection waters for waterflooding) or the enhanced oil recovery techniques that are to be performed in the field.

SUMMARY OF THE INVENTION

In one possibility there is provides an apparatus for injecting fluids into a plurality of samples of porous media, comprising: a plurality of holders for the samples of porous media, each holder comprising a sleeve and first and second platens, the first platen having an inlet for an injection fluid and the second platen having an outlet for a produced fluid, and the samples of porous media being arranged, in use, in each of the holders such that the first platen and second platen of each holder contact a first and second end of the sample of porous medium respectively, the inlet of each first platen being in fluid communication with an injection line for injecting fluid into the sample of porous medium arranged in the holder, the outlet of each second platen being in fluid communication with a dedicated effluent line for removing fluid produced from the sample of porous medium arranged in the holder, an analyzer for analyzing the fluids injected and/or removed from each of the samples of porous media.

In some possibilities the apparatus comprises a control system coupled to receive measurement data from the analyzer and configured to control the injection of fluid based on the measurement data. In some possibilities controlling the injection of fluid based on measurement data comprises controlling injection of fluid into one of the plurality of samples of porous media based on measurement data associated with another one of said plurality of samples of porous media. In some possibilities the control system is configured to control the apparatus to perform simultaneous concurrent injections which commence in a staggered fashion (e.g. with an onset delay between injections) these examples of the invention have the advantage that experimental data from the first experiments in a trial can be used to inform/control procedure before all the experiments have been completed. In addition resources such as fluid pumps, reservoirs and analysers can be shared between experiments. For example, if all the samples are set going at the same time it may be necessary to provide one complete set of all relevant apparatus for each experiment because they will all be at the same stage on a given date. In addition, the inventors in the present case have recognized that configuring the apparatus to start experiments in a staggered fashion enables fault detection and so increases throughput by enabling problems to be detected early thereby reducing the number of days lost to faulty experiments.

In some possibilities the apparatus comprises a fluid supply operable to control the supply of fluid for injection into the samples of porous media, wherein the control system is configured to control the fluid supply to at least one of said plurality of samples of a porous medium based on the measurement data.

In some possibilities the measurement data is based on the quantity of oil in the fluid removed from the sample of porous medium arranged in the holder. In some possibilities the controller is configured to stop the injection of fluid into one of said plurality of samples in the event that the quantity of oil in the fluid removed from the one of said samples is less than a selected threshold level. These and other examples of the invention have the advantage that, where many experiments are conducted trials can be stopped promptly when they are complete to enable the holder to be used for another trial, thus increasing the throughput of the apparatus.

In some possibilities the selected threshold level is one of: a selected concentration; a selected percentage by volume; and a selected percentage by mass of the fluid.

In one possibility there is provided a core flood testing method for injecting injection fluid into a plurality of samples of porous media, the method comprising: arranging a plurality of samples of porous media in respective ones of a corresponding plurality of pressure vessels, wherein the samples of porous media comprise oil and water at an initial water saturation, Swi, ageing the samples of porous media such that the samples are in a mixed wettability state; injecting an injection fluid into each of the samples of porous media, removing fluid displaced from the samples of porous media, analyzing fluids displaced from each of the samples of porous media.

In some possibilities analyzing comprises determining the amount of oil in a fluid displaced from one of the plurality of samples of porous media, the method comprising controlling the injection of fluid based on said determining.

In some possibilities controlling the injection of fluid comprises stopping injection of fluid in the event that the amount of oil in fluid displaced from the one of the plurality of samples is less than a selected threshold level. In some possibilities the method comprises, in response to said determining, removing said one of the plurality of samples of porous media from the pressure vessel and replacing said one of the plurality of samples with another sample comprising oil and water at an initial water saturation, Swi.

In some possibilities the method comprises injecting fluid into said plurality of samples for a selected period of time, wherein at least two of the samples are injected with fluid having different properties; ending the injection after the selected period of time has elapsed; based on said analysis selecting properties of a plurality of injection fluids; and injecting said plurality of injection fluids into a second plurality of samples. In some examples a control system of the apparatus referred to above is configured to control the apparatus to perform this function. These and other examples of the invention have the advantage that, based on an initial trial of a set of fluids, the trial protocol can be adjusted without human intervention to identify features and effects of interest.

In some examples the method comprises, prior to arranging the plurality of samples of porous media in the corresponding plurality of vessels; saturating the plurality of samples of porous media with water; and displacing water from the samples to achieve a selected level of water saturation, Swi, of the samples; wherein said arranging a plurality of samples of porous media in respective ones of a corresponding plurality of pressure vessels comprises transferring the plurality of samples at a selected level of water saturation to said corresponding plurality of pressure vessels. In some possibilities displacing water to achieve a selected level of water saturation, Swi, comprises one of: injecting a non-wetting phase into said samples; or centrifuging said samples under a non-wetting fluid. In some possibilities simultaneously injecting comprises providing a delay between the onset of at least some of the injections.

Water saturation/wetting as used herein generally includes wetting/saturation with any aqueous fluid such as brine. Similarly references to water should be taken to include brines, formation water or any other aqueous solution comprising water.

Described herein are a method and apparatus that can be employed as part of a high throughput research program to rapidly screen and rank a plurality of potential waterflooding or enhanced oil recovery methods for an oil-bearing reservoir thereby allowing the injection water for the waterflood or the injection fluid for the enhanced oil recovery method to be optimized based upon various parameters such as the chemical and physical characteristics of the reservoir rock, the chemical characteristics of the formation water associated with the reservoir rock, the chemical and physical characteristics of the oil, the chemical or physical characteristics of the injection water to be used in the waterflood or the chemical or physical characteristics of the injection fluid that is to be used in the enhanced oil recovery method.

Also disclosed is a process of ageing core samples in parallel thereby speeding up the acquisition of data.

The present invention also provides a method and apparatus that allows the determination of the relative permeabilities of a plurality of core plug samples to both oil and water in parallel thereby speeding up the acquisition of this data.

Described herein is an apparatus for simultaneously injecting fluids into a plurality of samples of porous media, comprising:

a plurality of holders for the samples of porous media, each holder comprising a sleeve and first and second platens, the first platen having an inlet for an injection fluid and the second platen having an outlet for a produced fluid, and the samples of porous media being arranged, in use, in each of the holders such that the first platen and second platen of each holder contact a first and second end of the sample of porous medium respectively, the inlet of each first platen being in fluid communication with an injection line for injecting fluid into the sample of porous medium arranged in the holder, the outlet of each second platen being in fluid communication with a dedicated effluent line for removing fluid produced from the sample of porous medium arranged in the holder, on-line and/or off-line analytical means for analyzing the fluids injected into each of the samples of porous media, on-line and/or off-line means for analyzing the fluids removed from each of the samples of porous media. As will be understood by the skilled reader in the context of the present disclosure, the duration of the core flood experiments described is typically on the order of days or tens of days so precise simultaneity is not required. Therefore, as used herein the term simultaneous is generally used to mean that tests are carried out concurrently or in parallel, e.g that the "simultaneous" tests are in progress at the same time, even though they may start and finish at different times.

There is further disclosed a method for simultaneously injecting injection fluid into a plurality of samples of porous media, the method comprising:

injecting an injection fluid into each of the samples of porous media, removing any fluid displaced from the samples of porous media, analyzing the fluids injected into each of the samples of porous media, and analyzing any fluids removed from each of the samples of porous media.

Also described herein is a computer-implemented method for determining one or more operating modes of an apparatus arranged to simultaneously inject one or more injection fluids into a plurality of samples of porous media, the method comprising the steps of:

receiving measurement data associated with one or more characteristics of the one or more injection fluids and/or one or more characteristics of the porous media and/or one or more characteristics of one or more fluids that are present within a pore space of the porous media prior to injection of the one or more injection fluids;

inputting said measurement data into a computer-implemented software component;

executing the software component so as to generate data indicative of one or more effects of injecting the one or more injection fluids into the plurality of samples; and determining, on the basis of the generated data, said one or more operating modes of the apparatus.

Described herein is a determination of the effects of injecting fluid(s) into a plurality of samples of porous media by generating data indicative of the effects, such as fluid release profiles, based on measurement data taken before, during and/or after the fluid injection.

Also described herein is a computer-implemented method for determining one or more operating modes of an apparatus arranged to simultaneously inject one or more injection fluids into a plurality of samples of porous media, the method comprising the steps of:

receiving data indicative of one or more effects of injecting the one or more injection fluids into the plurality of samples;

inputting said data into a computer-implemented software component configured to compare said one or more effects to a required effect;

executing the software component so as to generate experimental design data associated with obtaining the required effect, the experimental design data being indicative of a change to:

one or more characteristics of the one or more injection fluids; and/or one or more characteristics of the porous media; and/or one or more characteristics of one or more fluids that are present within a pore space of the porous media prior to injection of the one or more injection fluids; and determining, on the basis of the experimental design data, said one or more operating modes of the apparatus.

There are also described herein methods to provide appropriate algorithms of the experimental design component to devise further experiments having optimized characteristics, based on a comparison of known effects of performing an injection and a desired or preferred effect, such as an improved volume of the incremental oil recovered by the fluid injection.

DETAILED DESCRIPTION OF THE INVENTION

Apparatus

Figure 1:
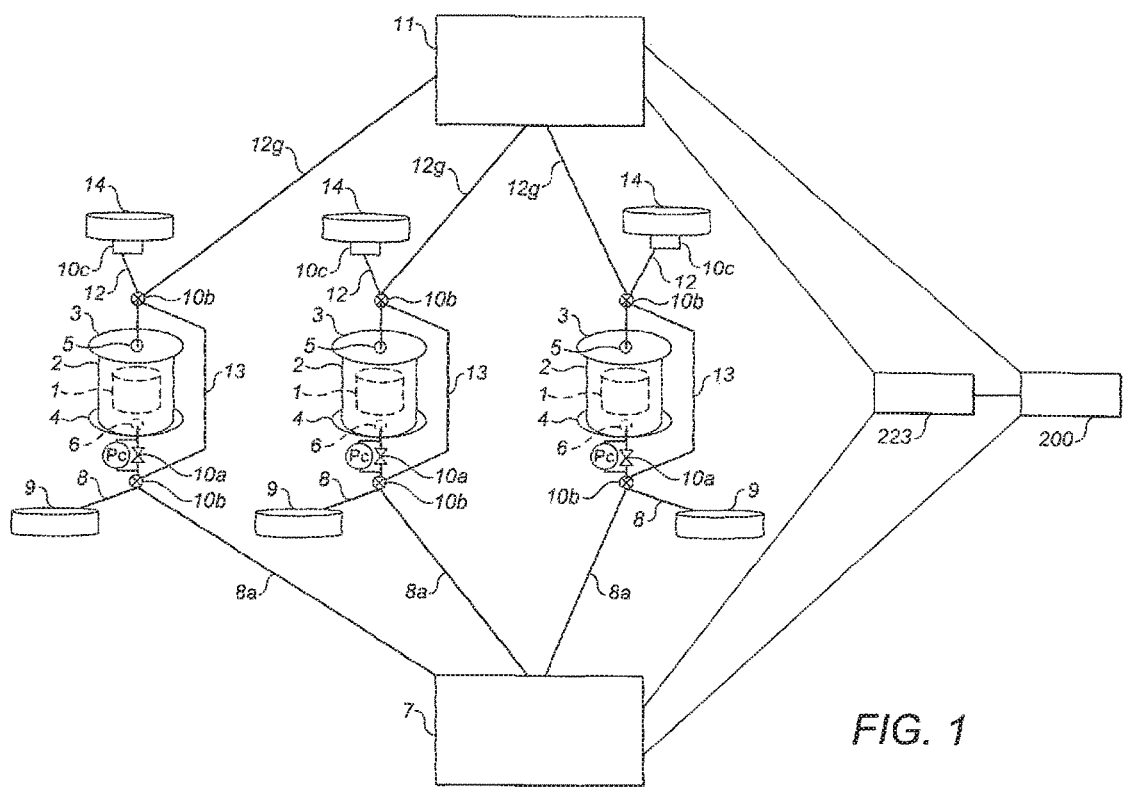
FIG. 1 is a schematic diagram of a high throughput apparatus according to the present invention.

FIG. 1 shows a high throughput apparatus for simultaneously performing flooding experiments on multiple samples 1 of porous media. FIG. 1 shows three samples 1 each contained in a dedicated pressure containment holder 2. However, the number of samples and holders 2 is not critical. Typically, each experiment is performed in duplicate, preferably, in triplicate, in order to test for reproducibility. For example, by providing eighteen samples 1, six sets of experiments may be performed in triplicate.

Typically, the holders 2 comprise first and second platens 3, 4 at the first and second ends thereof. FIG. 1 shows the holders 2 arranged vertically with inlets 5 and outlets 6 of the holders located on the first (upper) and second (lower) platens 3, 4 respectively. However, it may be preferred that the inlets 5 and outlets 6 are located on the second (lower) and first (upper) platens 3,4 respectively such that fluids are injected into the porous samples against gravity. Alternatively, the holders 2 may be arranged horizontally in which case, the location of the inlets 5 and outlets 6 is immaterial. Preferably, the inlets 5 and outlets 6 are located centrally on the platens.

Each effluent line 8 is connected to a respective fluid outlet 6 of each holder 2. The effluent lines 8 are preferably in fluidic communication with effluent collection vessels 9 for storing the fluids produced from the samples 1 of porous media. Typically, a dedicated pressure regulator 10a, for example in the form of a valve, is provided in each of the effluent lines 8 for regulating the pressure within the sample 1 of porous medium, for example, a back-pressure regulator.

A feed line 12 is also connected between a fluid source, for example, a reservoir 14 containing fluid, and the inlet 5 of each of the holders 2, such that fluid can flow through the feed line 12 from the source 14, into the holder 2 via the inlet 5, through the sample 1, and out of the holder 2 through the outlet 6 and effluent line 8 to the effluent collection vessel 9. Suitably, the apparatus is provided with a means for controlling the rate at which fluid flows through the feed line from the source and into the holder.

One or more on-line analytical instruments 7 may be provided for analysis of effluent fluid flowing from each sample 1. Suitable analytical techniques and instruments for use with the apparatus of the present invention are discussed in more detail below. It is envisaged that a sample of effluent fluid flowing from each sample 1 can be directed to the analytical instrument(s) 7. Alternatively, the analytical instrument(s) 7 may comprise at least one probe, sensor, or detector that is located on the effluent line 8 thereby allowing direct analysis of the fluids flowing through the effluent line 8. If necessary, a port may be provided in the effluent line 8 such that the probe, sensor, or detector may be located within the effluent flow (for example, a pH probe or ion selective probe) or a window may be provided in the effluent line 8 with the probe, sensor, or detector located adjacent to the window for interrogating the fluids flowing through the effluent line 8 (for example, for spectroscopic analytical techniques). For example, in the case of infrared (IR) analysis, the effluent flow may be irradiated with IR radiation produced by an IR source and an IR detector may be used to detect infrared radiation that is transmitted through the flow (i.e. is not absorbed by the effluent flow). In this case, the analytical instrument may be a Fourier Transform (FT) IR analytic instrument that generates a transmittance or absorbance spectrum showing the wavelengths at which the effluent fluid absorbs IR radiation. Accordingly, windows that are transparent to IR radiation (for example, a sapphire or quartz window) are provided in the effluent line for both the IR source and the IR detector. The use of probes or detectors enables the number of analytical instruments for each detection technique to be minimized, for example, a single IR analytical instrument may be used to generate IR spectra from data acquired using detectors located on two or more of the effluent lines 8.

Similarly, one or more on-line analytical instruments 11 may also be provided for analysis of fluids flowing through the feed lines 12. It is envisaged that a sample of fluid being fed into each sample 1 can be directed to the analytical instrument(s). Alternatively, the analytical instrument(s) 11 may comprise at least one probe, sensor, or detector that is located on the feed lines 12 thereby allowing direct analysis of the fluids flowing through the feed lines 12 using the techniques described above in respect of the effluent lines 8.

Multi-way valves 10b are provided in the feed lines 12 and effluent lines 8, and these valves 10b can be opened and closed as appropriate to allow fluid samples to be passed to analytical instruments 11 and 7 respectively via sampling lines 12g and 8a respectively. Sampling of the fluids may occur periodically such that samples from the flow lines 12 and from the effluent lines 8 are passed, in turn, to the analytical instruments 11 and 7 respectively. Hydraulic pumps 10c may also be provided for supplying the fluids from the source 14 to the feed lines 12.

The apparatus of FIG. 1 is provided with by-pass lines 13 that connect between the feed lines 12 and effluent lines 8. Each of the holders 2 (containing the samples 1 of porous media) may be shut in using multi-way valves 10b located on the feed lines 12 and effluent lines 8, thereby allowing for flushing out of the feed lines 12 and effluent lines 8 via by-pass line 13 (when switching between fluids). If desired, multi-ways valves 10b may be replaced with dedicated valves for the sampling lines 12g and 8a and dedicated valves for shutting in the holders 2 and directing fluids into the by-pass lines 13. Shutting-in of the holders 2 also allows each holder 2 to be removed from the apparatus for analysis of its associated sample of porous medium, for example, by NMR spectroscopy. Thus, the holders 2 may be designed to be readily removable from the high throughput apparatus, for example, by means of snap-fittings or quick-release fittings or compression-type fittings (not shown).

Optionally, further valves are provided in the effluent lines 8 such that when fluids are being flushed through the injection and effluent lines 12, 8 via the by-pass lines 13, the fluids pass to a waste collection vessel (not shown).

In order to avoid complexity, for each set of holders (used for performing experiments in duplicate or triplicate), it is preferred to feed the same fluids to each of the samples 1 contained in the holders and to switch between supplying different fluids substantially simultaneously.

Figure 3:
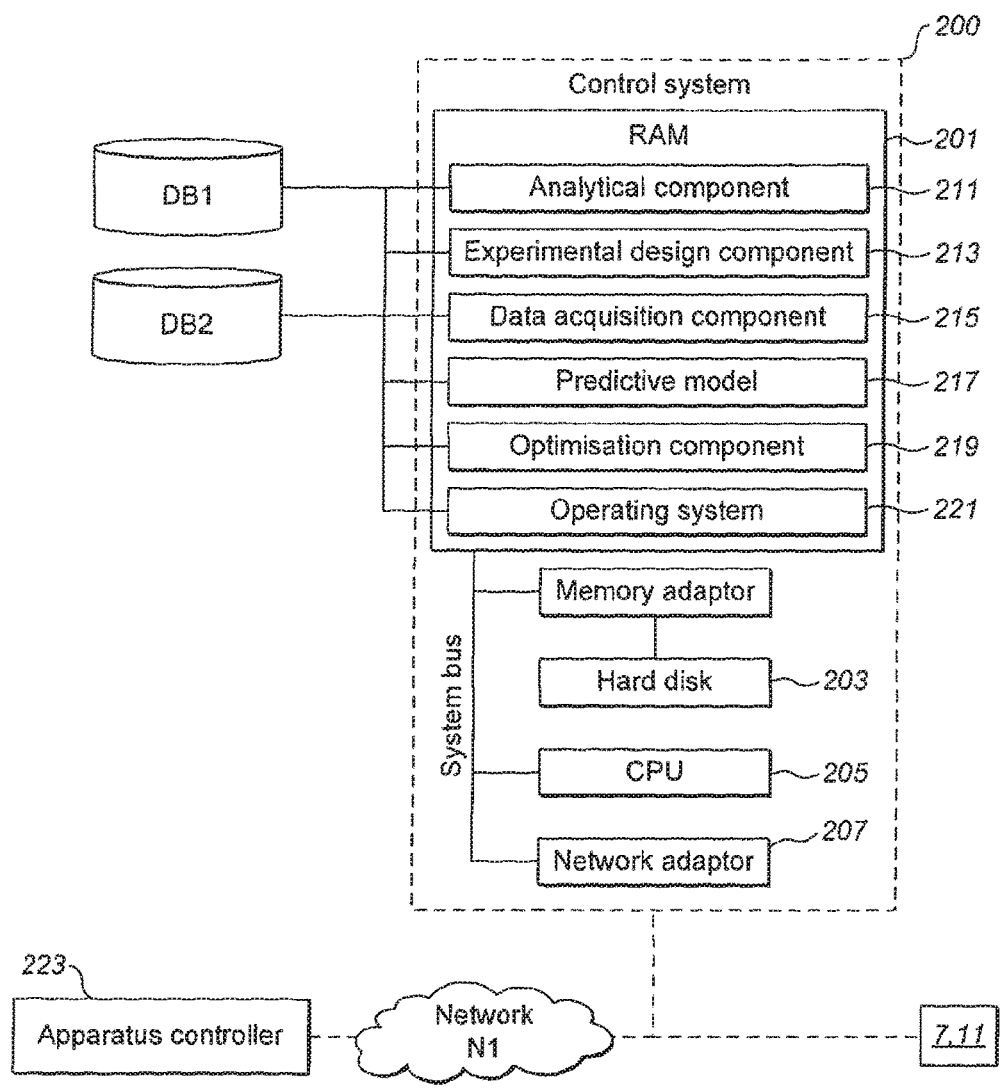
FIG. 3 shows a control system for determining one or more operating modes for a controller arranged to control the apparatus of FIG. 1.

The analytical instruments 7, 11, back pressure regulators 10a, flow control valves 10b, and pumps 10c are connected to a control system 200 and apparatus controller 223, as described further below with respect to FIG. 3.

Preferably, the holders 2 are cylindrical such that the holders 2 are suitable for holding cylindrical samples 1 of porous media. Preferably, the inlets 5 and outlets 6 of the first and second end platens 3, 4 are arranged substantially centrally thereby ensuring uniform injection of fluid into the samples 1 of porous media.

The pressure containment holders 2 may be formed, for example, from stainless steel, a plastics material such as Teflon™ or Polyether Ether Ketone (PEEK) polymers, or from carbon fibre. Where it is intended to periodically analyze the samples of porous media using NMR spectroscopy, the sample holders 2 should be formed from a non-metallic material, for example, a plastics material or from carbon fibre.

Typically, each of the samples 1 of porous media are provided with a rubber sleeve (not shown) that is open at each end. O-rings (not shown) may be provided at each end of the rubber sleeve for forming a fluid tight seal with the pressure containment holder 2 such that a fluid tight annulus is formed between the outer surface of the rubber sleeve and the inner surface of the pressure containment holder 2. Typically, each holder 2 is provided with an inlet and outlet (not shown) for a pressurized fluid such that the pressurised fluid can be passed into the annulus and thereby exert an overburden pressure on the sample 1 of porous medium. Typically, the overburden pressure is in the range of 350 to 5000 psi, for example, about 400 psi.

The number of samples 1 of porous and permeable media that may be tested simultaneously (in parallel) using the high throughput apparatus of the present invention is dependent upon the number of holders 2. Typically, the apparatus may comprise 6 to 100, preferably, 12 to 75, for example, 12 to 32 holders.

The samples 1 of porous media should be permeable to the fluids that are injected into the samples 1. Typically the samples 1 of porous media may be plugs taken from one or more core samples removed from a hydrocarbon bearing formation of a reservoir that is under investigation or from an outcrop rock having similar physical and chemical characteristics to the formation rock of the reservoir under investigation. Typically, the core samples may be taken from a sandstone formation or from a carbonate formation (or a sandstone or carbonate outcrop rock).

When a plurality of core plugs are to be compared using the high throughput apparatus and method of the present invention, it is preferred that the core plugs are drilled in close proximity from a core sample and are therefore expected to have similar rock properties (chemical and physical characteristics). Such plugs are referred to as "sister plugs". However, the apparatus and method of the present invention may also be used to compare core plugs from core samples taken from different locations of a reservoir to determine whether differences in rock characteristics across the reservoir have an impact on waterflooding or enhanced oil recovery (EOR) techniques.

Alternatively or additionally, the samples of porous media may comprise sandpacks, preferably formed from produced sand; packs of ion exchange resin particles (either cationic or anionic exchange resins) that are designed to mimic ion exchange between injection fluids (in particular, injection waters) and the rock surface at the reservoir scale; packs of hydrophilic or hydrophobic resin particles (that are designed to mimic hydrophilic or hydrophobic surface of the formation rock); synthetic rock (e.g. silica); zeolites; or ceramic materials. Clays (for example a kaolinite, smectite, pyrophyllite, illite, chorite or glauconite type clay) may be mixed with a sand prior to forming a sandpack. Clays may also be deposited onto sandpacks or onto synthetic rock samples. For example, cemented quartz may be bound with calcite and clays may then be deposited onto the surface of the synthetic rock.

The size of the samples 1 of porous media depends on the oil detection limit. If the detection limit of oil in water is very low then the size of the sample 1 may be very small. Currently the detection limit for oil in water is 0.1 ml of oil in 10 ml of water. If it is desired to detect a 1% increase in oil recovery, this requires the sample to have a minimum accessible pore volume to oil of 10 ml. However, for rapid screening purposes a minimum detection limit of a 5% increase in oil recovery (incremental oil recovery) may be acceptable. Typically, the samples 1 of porous media are cylindrical in shape, preferably having a diameter in the range of 1 to 3 inches, more preferably, 1 to 2 inches, for example 1 to 1.5 inches and a length in the range of 1 to 6 inches. For each set of experiments, the samples 1 of porous media are of substantially identical size.

The samples 1 of porous media are preferably loaded into each of the plurality of holders 2 of the high throughput apparatus. However, it is possible that one or more of the holders 2 are off-line, for example, for maintenance. As discussed above, the holders 2 may be arranged either horizontally or vertically in the apparatus such that fluids either flow through the samples in a horizontal direction or vertical direction. It is preferred that aqueous fluids (e.g. formation water, injection water) flow in a vertical direction from a lower to an upper end of each sample 1. In the case of oil injection, it is preferred that the flow of oil in the vertical direction is from a lower to an upper end of each sample (in which case the oil may be injected into each sample 1 through the outlet of the holder 2).

Typically, the fluids contained within the pore space of the porous media (for example, formation water and oil) for each of the parallel sets of experiments are the same but the injection fluid may vary. However, it is also envisaged that the injection fluid employed for each experiment may be the same and that one or more of the samples 1 of porous media, the oil or the formation water may be varied.

Although shown as disc shaped members in the drawings this is merely schematic. As will be appreciated by the skilled reader in the context of the present disclosure the platens need not have a particular shape and certainly need not be plate like. A function of the platens is to enclose a test sample in a pressure vessel for testing and, optionally, to allow fluids to enter and leave the vessel and, further optionally to apply pressure to the sample. In particularly advantageous examples one or both of the platens may be provided by plungers. The two platens need not be similar to each another.

Figure 2A:
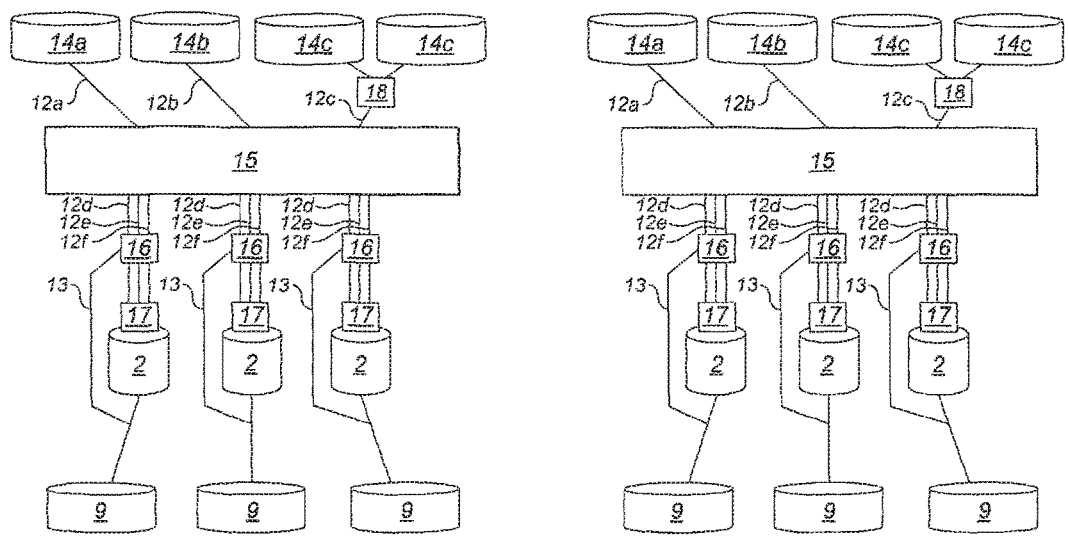
FIGS. 2a and 2b shows schematic diagrams of examples of a fluid flow line arrangement used in the apparatus of FIG. 1.

FIG. 2a shows a detailed example of the flow lines and manifolds that may be employed by the apparatus of FIG. 1. In the example of FIG. 2a, two sets of three holders 2 are shown; however, the apparatus may have additional sets of holders, for example, an additional four to ten sets of three holders. For simplicity, the sample 1, platens 3, 4, inlet 5 and outlet 6 for each holder are not shown.

In order to avoid any contamination of fluids, it is preferred that there is a dedicated reservoir 14a, 14b, 14c for each fluid. If dedicated reservoirs are not provided, it will be necessary to thoroughly clean the reservoir prior to switching fluids.

A main oil feed line 12a is connected from an oil source 14a to a main manifold 15. Dedicated oil feed lines 12d (one per holder 2) lead via bypass manifolds 16 to input manifolds 17 for each of the holders 2. Similarly, a main formation water feed line 12b for the formation water is connected from a formation water source 14b to the main manifold 15, and dedicated formation water feed lines 12e (one per holder 2) lead via the bypass manifolds 16 to the input manifolds 17 for each of the holders 2.

In the example of FIG. 2a, a plurality of injection fluid sources 14c (two of which are shown) may be provided, in fluidic communication with an injection fluid manifold 18 which allows fluidic communication between one of the injection fluid sources 14c and the main manifold 15 via a main injection fluid feed line 12c. For example, when a plurality of porous samples 1 are to be flooded in tertiary mode, a synthetic seawater or a synthetic low salinity water may be stored in the first fluid source 14c and the injection fluid (for example, injection water) that is under investigation may be stored in the second fluid source 14c. Dedicated injection fluid feed lines 12f (one per holder 2) lead via the bypass manifolds 16 to the input manifolds 17 for each of the holders 2. Typically, the input manifolds 17 are arranged on the first platen 3 of each holder 2.

Hydraulic pumps (not shown) may be provided in the flow lines. Valves (not shown) may also be provided in the flow lines and/or at the bypass manifolds 16 and input manifolds 17 as appropriate to allow switching of fluids.

The input manifolds 17 operate to allow different fluids to be fed in a pre-determined sequence (that may be controlled by the experimental design software component of the high throughput apparatus) into the inlet 5 of the first platen 3 of the holder 2. The by-pass lines 13 are provided such that the main feed lines 12a, 12b, 12c and dedicated feed lines 12d, 12e, 12f can be flushed by being connected directly to the effluent line 8 when the feeds are to be switched between different fluids.

Valves in the main feed lines 12a-c may be opened or closed to allow selected fluids to flow into the main manifold 15, into the appropriate dedicated feed conduits 12d-f, into the input manifolds 17 and into the samples 1. Suitably, the control system (discussed below) of the high throughput apparatus ensures that the correct sequence of opening and closing of the valves. For unsteady state flooding experiments, the control system ensures that single fluids are injected in the correct sequence into the input manifolds 17. For steady state flooding experiments (for example, steady state relative permeability experiments) a mixture of oil and water may be injected into the samples 1. The control system ensures that the mixture of oil and water is injected simultaneously into the samples 1 in the desired ratio (by controlling both the correct sequence of opening and closing of the valves and through adjustment of the flow rates of the oil and water).

Figure 2B:
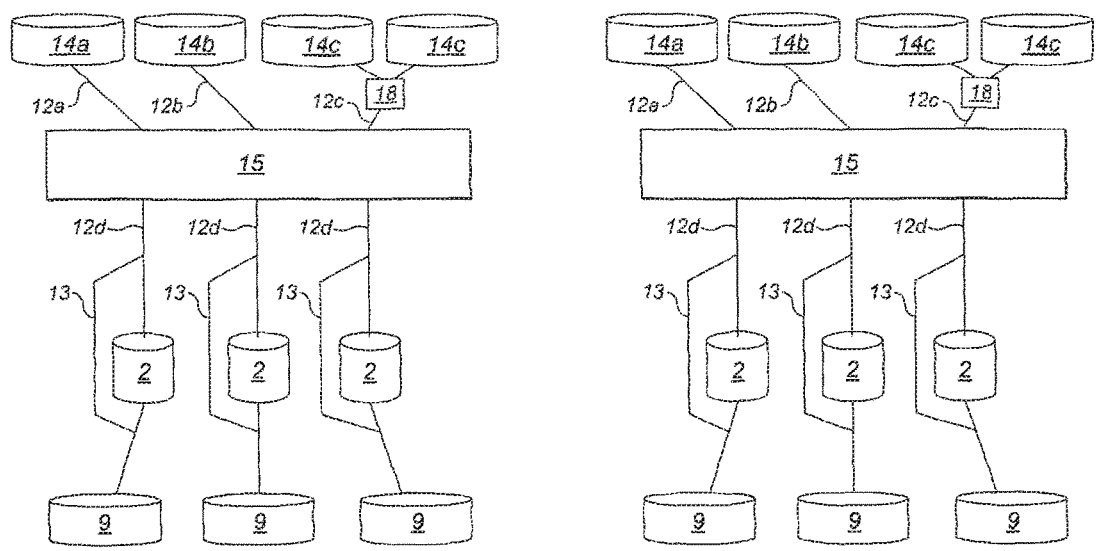

Other arrangements for supplying fluids to each of the holders 2 may be envisaged. An example of an alternative arrangement is shown in FIG. 2b where valves (not shown) in the feedlines 12a, 12b, and 12c may be opened or closed to allow selected fluids to flow into the main manifold 15 and into a single dedicated feed line 12 for each holder 2. The single dedicated feedlines 12 are each provided with a by-pass line 13 that allows for flushing of the main manifold 15 and the dedicated feed line 12 thereby avoiding contamination of the samples 1.

Irrespective of the arrangements for supplying fluids to each of the holders 2, the samples 1 of porous media are typically heated to the desired experimental temperature, for example, the temperature of the reservoir under study. Heating of the samples 1 to the desired temperature may be achieved by arranging each holder 2 (containing a sample 1 of porous medium) in a dedicated oven. Alternatively, each of the holders 2 may be provided with a dedicated heating jacket. These arrangements allow the temperature of the samples 1 to be individually adjusted. If it is desired to heat the injection fluid to the desired experimental temperature prior to it being injected into the samples 1 of porous media, the feed line 12 (or dedicated feed line 12d,12e,12f) is also preferably heated (for example, the final portion of the feed line 12 may be located in the oven or the final portion of the feed line 12 may be provided with a heating jacket. If desired, some or all of the holders may be arranged within a single oven. For example, a set of holders 2 (and their porous samples) that are to be used to perform experiments in duplicate or triplicate may be heated to the desired experimental temperature by arranging the set of holders 2 within a single oven.

Where the samples 1 of porous media are core samples, the simultaneous coreflood experiments may be performed with the samples 1 placed under full reservoir conditions, that is, the pressure and temperature of the reservoir from which the core samples were taken; however, if desired the coreflood experiments may be performed at reservoir temperature but at a more suitable laboratory pressure. Typical reservoir temperatures are in the range of 20 to 150° C., for example, 40 to 90° C. Suitable laboratory core pressures are in the range of 4 and 50 bar absolute, preferably, 10 to 20 bar absolute, for example, about 15 bar absolute. However, the cores should be maintained at a sufficiently high pressure to prevent gas break-out (dissolved gas forming a separate gaseous phase in the core), in particular, when using live crude oils.

Where mechanistic studies are being undertaken using sandpacks, synthetic rocks, packs of resins, zeolites or ceramic materials, the samples of porous media may be maintained at a temperature in the range of 20 to 90° C. and at a suitable laboratory pressure (for example, at a laboratory pressure as described above for the coreflood experiments).

Analysis of Samples of Porous Media and of Fluids

Preferably, the high throughput apparatus is provided with a means for analyzing samples of the fluids that are injected into the porous samples for determining one or more chemical or physical characteristics of the fluids. These fluids include cleaning solvents, formation water, oil, and the injection fluids that are under investigation (i.e. the injection waters used in simultaneous waterflood experiments or the injection fluids used in simultaneous enhanced oil recovery experiments). The chemical or physical characteristics of these fluids may be determined off-line or on-line. Where off-line analysis is performed, samples of the fluids are taken for subsequent analysis. Preferably, the apparatus is also provided with a means for analyzing samples of fluids produced from the porous media (typically oil and brine) for determining one or more chemical or physical properties of the produced fluids.

The apparatus may also be provided with a means for analyzing the samples 1 of porous media (for example, core samples) for chemical and physical characteristics.

One or more analytical systems or instruments may be used to determine the composition of fluids injected into the samples of porous media and the fluids produced from the samples 1 of porous media to obtain data relating to the chemical and/or physical characteristics of the injected fluids and of the produced fluids. Although manual or semi-automated chemical analysis systems are possible, preferably an automated system, as described below with respect to FIG. 3, is employed to control and analyse the data acquired using the analytical system(s) or instrument(s). The analytical system(s) or instrument(s) typically comprise a sensor, probe or detector and hardware for detection of signals produced by the sensor, probe or detector. For spectroscopic techniques, the analytical system(s) or instrument(s) typically also comprises a source of electromagnetic radiation (for example, ultraviolet, visible, or infrared radiation).

Preferably, sampling points are provided immediately upstream and immediately downstream of the holders 2. Both on-line and off-line analytical techniques may be employed. For on-line analytical techniques, a sensor, probe, or detector of an analytical instrument 7, 11 may be located directly on the pipework of the high throughput apparatus at each of the sampling points, for example, immediately before the inlets 5 or after the outlets 6 of the holders 2. As discussed above, the sensor, probe or detector may be located in the flow of fluid or adjacent to a window in the pipework such that the sensor, probe or detector can acquire analytical data in respect of fluids flowing through the pipework. Alternatively, it may be possible to automate the high throughput apparatus such that at least a portion of the flow of fluid to each of the holders 2 or at least a portion of the produced fluids or effluent removed from each of the holders 2 is diverted in sequence to an analytical instrument 7, 11 such that the analytical instrument 7 sequentially analyses the fluids that are being fed to each of the samples of the porous media and/or the analytical instrument 7 sequentially analyzes the produced fluids or effluent being removed from each of the samples 1 of porous media. For example, a selector valve can selectively pass effluent fluids from one of the effluent lines 8 to the analytical instrument 7 via sampling lines 8a. Similarly, a selector valve can selectively pass injection fluids from one of the feed lines 12 to the analytical instrument 11 via sampling lines 12g. A number of different on-line analytical instruments may be employed for analyzing different characteristics of the fluids. For off-line analytical techniques, the high throughput apparatus may be automated such that samples of fluids are removed at regular intervals via sampling ports for off-line analysis.

Analytical techniques for use with the high throughput apparatus of the present invention include chromatographic techniques and spectroscopic techniques. Suitable chromatographic techniques include gas chromatography (GC), high pressure liquid chromatography (HPLC), or ion chromatography used for detection of anions or cations. Suitable spectroscopic techniques include mass spectroscopy (MS) such as atomic emission spectroscopy, atomic absorption spectroscopy, Fourier Transform Mass Spectroscopy (FT-MS), Fourier Transform ion cyclotron resonance mass spectroscopy (FT-ICR-MS) and gas chromatography-mass spectroscopy (GC-MS); infrared (IR) spectroscopy; near infrared (NIR) spectroscopy; Raman spectroscopy; ultraviolet (UV) spectroscopy and ultraviolet-visible (UV-VIS) spectroscopy including the use of fluorescent markers or chromophores that interact with the chemical component that is to be detected to produce a signal in the UV or visible region of the electromagnetic spectrum, for example, ionophores are available that react with specific cations or anions thereby allowing detection of these cations or anions using fluorescence or a colour change; nuclear magnetic resonance (NMR) spectroscopy, and electron spin resonance (ESR) spectroscopy. Other techniques include ion selective probes that may be used to determine the total dissolved solids content of a sampled water or of water flowing through a flow line (for example, formation, injection water, or water produced from the cores) or to detect specific ions in the sampled water or water flow, inductively coupled plasma (ICP) for the detection of metal ions; pH probes, sensors that detect electrical properties such as impedance, resistance, dielectric constant or the like, and nephlometry for determining the oil content of produced fluids. Nephlometric techniques involve measuring the turbidity of a liquid sample by analysis of light scattering in the liquid sample. Many of these techniques may be used on-line such as the chromatographic techniques listed above, and the following spectroscopic techniques, GC, HPLC, ion chromatography, IR, NIR, Raman, UV, UV-VIS and nephlometry. However, mass spectroscopic techniques will require sampling of the fluids, typically the oil, for off-line analysis while NMR analysis of the samples of porous media 1 will require the holders 2 to be periodically removed from the high throughput apparatus and placed in an NMR spectrometer.

Test Variables

The high throughput apparatus is capable of investigating one or more of the following variables:
different types of porous media;
formation water composition;
oil composition;
injection fluid type and composition (for example, injection water composition);
temperature (for example, reservoir temperature);
pressure (differential pressure across the porous samples and absolute pressure within the pore space of the porous samples);
compositions of produced fluids over time (for example, composition of produced water or composition of produced oil);
amount of oil produced over time and/or total amount of oil produced.
in the case of reservoir condition core floods that employ a "live" oil, gas-oil ratios and/or the composition of the gas.

The porous media samples 1 may be core plugs taken from samples of a hydrocarbon bearing formation of a reservoir including both sandstone and carbonate core plugs; plugs of outcrop rock; sandpacks including sandpacks formed from produced sand; resin packs, artificial rocks, ceramic materials, or zeolite materials.

As discussed in more detail below, for flooding experiments or enhanced oil recovery experiments, the samples of porous media are typically injected with formation water and then oil and are then preferably aged.

The formation water that is injected into the samples of porous media is typically the connate water (water that is originally in place in the reservoir). However, where the reservoir has been waterflooded, the formation water may have the composition of the water that is present in the reservoir under investigation (a mixture of connate water and previously injected water).

The oil that is injected into the samples 1 of porous media may be a stock tank oil (STO) taken from the reservoir of interest or a "live" oil (a STO recombined with gas, typically, a synthetic gas that is representative of the gas that is separated from the oil at a production facility). Synthetic oils may also be employed. For example, an organic solvent containing one or more components typically found in crude oil such as aromatic compounds, aliphatic compounds, acids, bases, or asphaltenes. The use of synthetic oils allows the study of the mechanisms by which different components of a crude oil are bound to the rock surface and also the mechanisms by which these components of the crude oil are displaced from the rock surface (or from the surface of an analogous material such as an ion exchange resin) to be studied. For example, interactions between the components of the crude oil and additives that are contained in an injection fluid can be investigated. Typically, the base organic solvent for the synthetic oil is selected from a $C_5$ to $C_{20}$ alkane, for example, pentane, hexane, heptane, octane, nonane, decane, undecane, dodecene and mixtures thereof. Alternatively an aliphatic base oil may be employed provided that this base oil does not contain aromatic hydrocarbons. An example of a suitable aliphatic base oil is depolarized kerosene.

The injection fluids that may be tested include base brines of varying total dissolved solids (TDS) content (salinity). For example, brines having a TDS in the range of 100 to 200,000 ppm may be tested. Other potential injection fluids that can be tested include steam and gases. The gases may be, in particular, miscible gases such as $CO_2$, hydrocarbon gases (such as methane, ethane or propanes) or mixtures thereof. Alternatively, the gases may be $N_2$, or air.

In the case of miscible $CO_2$ injection, the temperature and pressure of the $CO_2$ should be chosen such that the $CO_2$ is in a supercritical state. The injected supercritical $CO_2$ will be miscible with the oil that is present in the solid medium, thereby reducing the viscosity of the oil and sweeping out more oil from the sample 1. Owing to the $CO_2$ being miscible with the oil, it may be necessary to reduce the pressure of the effluent, to drive off gaseous $CO_2$ before determining the amount of oil produced. Measurement data indicative of, for example, an absolute and differential pressure, volumetric fluid recovery and the composition of fluid recovered, is taken. Such $CO_2$ floods typically involve relatively small volumes of fluid, and some produced fluid samples may have a volume of less than 0.2 $cm^3$. Miscible applications may take place over a wide range of temperatures and pressures, but a typical temperature is approximately 120° C. (~400K) and a typical pressure is approximately 300 bar. One example of a technique used in $CO_2$ flooding experiments involves bringing the produced fluids to reservoir temperature and pressure. The produced fluids are then "flashed" (reduced in pressure) though a regulator valve to atmospheric pressure and temperature. Fractional samples are then collected for compositional analysis by the analytical component 211 of the control system 200. The mass of each fraction is measured and then, using an original live crude oil density and formation pore volume factor, the fractional volume of oil at reservoir conditions can be determined.

Suitable additives for the injection fluid, in particular, for injection waters, include cations, anions, polymers, surfactants, alkalis, acids, microbes, colloids, clay particles, nanoparticles, microgel particles, polymer particles, and mixtures thereof.

Additives may be tested over a large concentration range to determine optimal concentrations, for example, concentrations in the range of 5 to 20,000 ppm.

Two or more additives may be included in the injection fluid to test for synergies between additives.

Formation damage of core plugs that may arise from passing an injection fluid through the core plugs may be measured by monitoring any changes in the differential pressure across the core plugs. Typically, an increase in the differential pressure is indicative of formation damage with the amount of formation damage being related to the ratio of the initial differential pressure across the core plug to the final differential pressure across the core plug (for the same fluid viscosity). It may also be necessary to monitor the viscosity of the fluid being injected into the core to correct for changes in differential pressure arising from different viscosities of the various injected fluids.

Method

Also disclosed herein is a method for simultaneously injecting injection fluid into a plurality of samples of porous media wherein the samples of porous media are saturated with oil at irreducible water saturation, $S_{wi}$, the method comprising:

ageing the samples of porous media that are saturated with oil at $S_{wi}$ such that the samples are in a mixed wettability state;

injecting an injection fluid into each of the samples of porous media, removing any fluid displaced from the samples of porous media, analyzing the fluids injected into each of the samples of porous media, and analyzing any fluids removed from each of the samples of porous media.

There is also disclosed herein a method in which, the samples 1 of porous media are substantially similar, for example in their mineral components, density, porosity and physical dimensions and, indeed may be identical. Similarly, the formation water and oil that are used to bring each of the samples 1 of porous media to irreducible water saturation are substantially similar or the same. Alternatively or additionally, the injection fluid that is employed in each of the simultaneous experiments may be substantially similar or the same, and one or more of the other variables can be changed/controlled, for example, the oil composition, formation water composition or the type of porous media The simultaneous experiments may be performed in secondary mode by injecting different test injection fluids into the samples 1 of the porous media. Alternatively, a baseline injection fluid, for example, synthetic brine is injected into each of the samples 1 to bring the samples 1 to a first residual oil saturation, $S_{or1}$. Different test injection fluids are then injected into the samples 1 of porous media in tertiary mode. If no incremental oil is produced in tertiary mode, the samples 1 remain at the first residual oil saturation. If incremental or additional oil is produced from the sample 1, the samples 1 are at a second lower residual oil saturation, $S_{or2}$. Preferably, the method of the present invention includes the determination of the first and second residual oil saturations (as described below). Preferably, each simultaneous experiment is performed in duplicate or triplicate by injecting a different test injection fluid into either two or three of the samples 1 of porous media respectively.

Control System Software

Generally, the automated system comprises the control system 200 that includes various programmable software components or tools; referring to FIG. 3, an analytical component 211 and an experimental design component 213 are provided, and further software components in the form of a data acquisition component 215, a predictive model 217 and an optimisation component 219 may be provided as described further below. The control system 200 comprises conventional operating system 221 and storage components such as a system bus connecting a central processing unit (CPU) 205, a hard disk 203, a random access memory (RAM) 201, I/O and network adaptors 207 facilitating connection to user input/output devices and interconnection with other devices, such as analytical instruments and/or the apparatus controller 223, as described below, optionally on a network N1. The RAM 201 contains operating system software 221 which controls, in a known manner, low-level operation of the processing system 200. Further, when controlling and/or analysing the injection of fluid into the samples 1 under control of the apparatus controller 223, the operating system 221 loads into RAM 201 software components 211, 213, 215, 217 and 219. Each software component 211, 213, 215, 217, 219 is configurable with the measurement data and/or predetermined data which can be stored in a database DB1, DB2 or other storage component that is operatively coupled or connected to the processing system 200.

As discussed below, the porous samples (in particular, core plug samples) are preferably cleaned prior to being saturated with oil at irreducible water saturation. The porous samples are then aged using an ageing protocol. One or more sets of flooding experiments are then performed by injecting an injection fluid into the samples 1. Measurements of characteristics of the fluids and porous media required for further analysis by the control system 200 may be taken before, during and/or after each of these cleaning, saturation, ageing and flooding stages, and at each stage a user or operator of the apparatus and control system 200 is optionally able to check the measurement data and manually instruct the apparatus and/or control system 200 to proceed to the next stage as desired.

Figure 4:
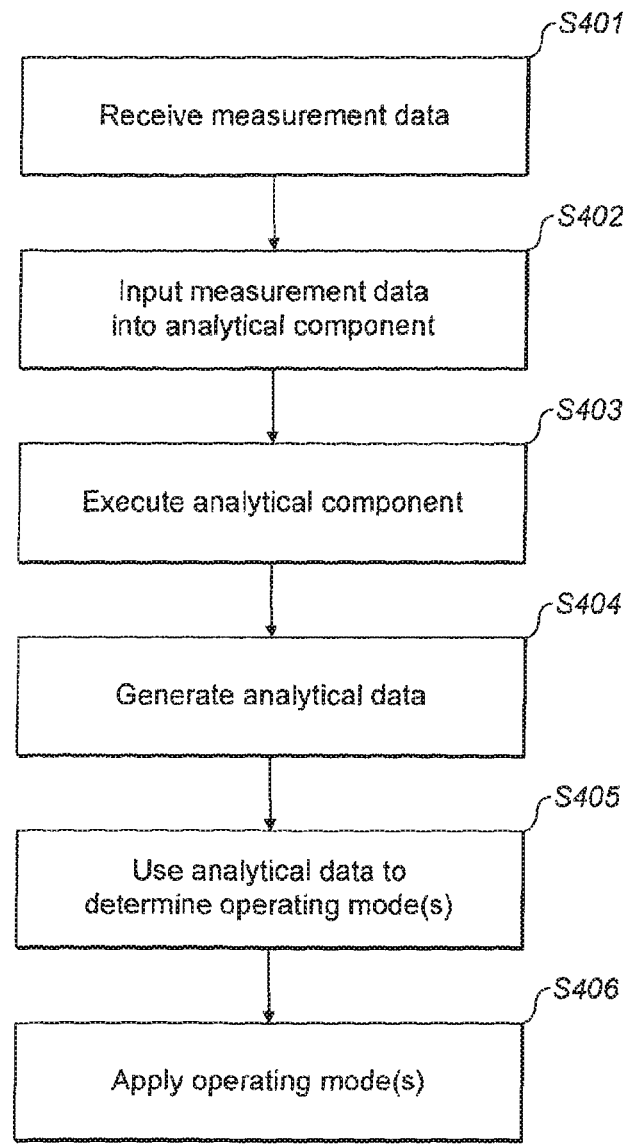
FIG. 4 shows the steps carried out in a method for determining one or more operating modes for the apparatus of FIG. 1 using an analytical software component.

Referring to FIG. 4, the steps involved in analysing measurement data received by the control system 200 from the analytical instruments 7, 11 and/or other data acquisition hardware are shown. The measurement data may comprise specific measured values as directly measured by the suitably positioned analytical instruments 7, 11. At step S401, the measurement data is received by the control system 200, preferably by the data acquisition component 215. The data acquisition component 215 may be configured to process the raw measurement data received to obtain ratios of values of characteristics, or values derived from a number of separate characteristic measurements, according to known techniques. Therefore, the raw measured characteristics may, if necessary or preferred, be manipulated by the data acquisition component 215, or alternatively by analytical component 211, in order to generate measurement data that are suitable for inputting, at step S402, into one or more particular calculation algorithms of the analytical component 211. Such manipulation may simply comprise a measurement unit conversion or the creation of a required ratio of measured values.

At step S403, the analytical component 211 executes according to predetermined rules, for example in the form of various algorithms (which are preferably stored in and accessible from the storage component DB1 as necessary and automatically executed according to the parameters of the data received). The analytical component 211 is configured to analyze the compositions of the various fluids and materials involved in the experiments, for example, data indicative of the chemical characteristics of the injection fluid to be used for each of the simultaneous experiments, and can also be configured to analyze experimental results received by the data acquisition component 215 of the control system 200. More specifically, the analytical component 211 is programmed according to rules such as protocols for cleaning the samples of porous media (discussed below), ageing protocols (discussed below) and analytical protocols for analyzing the injection fluids and produced fluids, so as to output data such as fluid release profiles and fluid composition parameters, as will be described with reference to step S404.

In step S404, the analytical component 211 generates, as output, analytical data, which is indicative of the effects of fluid injection based on the measurement data. The analytical data may comprise a produced fluid release profile based on each sample 1 (or a single produced release profile combining output data from similar samples); such fluid release profiles show changes in the composition and/or amount of the produced (recovered) oil and/or the composition of produced water over time. The analytical component 211 can determine, for example, when no further oil is being recovered from the samples; and when the composition of produced injection fluid (for example, produced water) flowing out of the samples is substantially the same as the composition of the injection fluid. The amount of incremental oil recovered from a sample based on a specific set of experimental parameters can also be determined by the analytical component 211.

The analytical component 211 can determine when the porous samples are clean, by detecting when cleaning solvents being recovered from the samples are of substantially the same composition as solvents injected into the samples, in particular, by detecting when components of oil are no longer present in the solvent that is being recovered from the samples. In addition, the analytical component can determine when the porous samples are saturated with brine at 100% water saturation, $S_w=1$, when the samples are at irreducible brine saturation, $S_{wi}$, and, when the samples are saturated with oil at $S_{wi}$ and the initial oil saturation, $S_{oi}$. For example, when injecting brine as an injection fluid, the samples 1 are determined to be at $S_{wi}$ when the presence of brine, preferably at above a predetermined threshold amount, is detected by the analytical instruments 7 in the effluent lines 8. The analytical component 211 may also determine when ageing of the porous samples (discussed below) is complete, for example, by analyzing NMR data that is obtained periodically for each of the porous samples. An interpretation of the measurement data may be made by the analytical component 211 based on a mapping between certain parameter values or ranges stored in a look-up table that is accessible by the analytical component 211.

Once the analytical component 211 has been executed and analytical data are generated, software executed by the CPU 205 of the system 200 determines at step S405, on the basis of the analytical data, one or more operating modes of apparatus controller 223. The analytical component 211 may be configured to determine the operating mode(s) upon generation and interpretation of the analytical data, or a separate software component (not shown) may be provided. As discussed above, the analytical data may comprise a fluid release profile showing changes in the amount of the produced oil over time (typically, the cumulative amount of produced oil over time), and this may be used by the analytical component 211 to determine a future operating mode for the apparatus controller 223 based on an interpretation of the profile by the analytical component 211. The analytical component 211 can access a look-up table to determine whether an operating mode should be applied to the apparatus controller 223 on the basis of this data.

For example, if analysis of the oil recovery profile shows a sharp increase in the volume of oil recovered (for example, if there is a marked increase in the gradient of the cumulative oil recovery against time profile or if the volume of oil produced is above a threshold value), the analytical component 211 may determine via the look-up table that the injection of the injection fluid currently in use should continue, and an operating mode comprising an instruction to continue injecting the injection fluid is sent to the apparatus controller 223. Alternatively, if analysis of the oil recovery profile indicates that there is either no oil recovery or an insignificant amount oil recovery after a predetermined volume of injection fluid (such as 30 PV (Pore Volumes, defined herein as the volume of the pore space of the sample 1 of porous media)) is injected, the look-up table may indicate that injection of the fluid should stop as it is not producing a sufficient volume of incremental oil, and the analytical component 211 will determine and apply a suitable operating mode, instructing the apparatus controller 223 to stop the current injection. The analytical component 211 may also recognise any inflection point present in the oil recovery profile, which indicates a point in time at which the incremental oil recovered begins to decline (for example, the cumulative oil recovery against time profile begins to plateau; in such a case, the analytical component 211 may determine an operating mode from the look-up table to continue the injection for a predetermined length of time, or to inject a predetermined volume of injection fluid such as 20 PV, after that time, and to then stop the injection of the fluid.

The operating mode is applied at step S406 by sending the operating mode to the apparatus controller 223, where the instruction is executed by control software associated with the controller 223. The control software allows, for example, remote actuation of the valves 10a, 10b and the pumps 10c. The control software is therefore configured with appropriate rules such that an appropriate pump 10c can be operated simultaneously to, or at an appropriate time period within, the opening of appropriate valves 10a, 10b.

The data acquisition component 215 may additionally or alternatively generate operating modes, for example in order to instruct the high throughput apparatus to divert samples of the fluid input and/or output from each of the holders 2, in turn, to analytical instruments 7, 11 for the determination of certain chemical and/or physical parameters. Where the analytical instrument comprises a plurality of sensors, detectors or probes that are located within the plurality of effluent lines 8 or adjacent to the plurality of effluent lines 8, the analytical component 211 or the data acquisition component 215 may generate operating modes to instruct the analytical instrument to record data that is being acquired by the sensors, detectors or probes for the determination of certain chemical and/or physical parameters. The analytical component or the data acquisition component 215 may instruct the analytical instruments 7, 11 to acquire this data either continuously or intermittently. It is envisaged that two or more different sensors, detectors or probes for two or more different analytical instruments may be located within an effluent line 8 for acquiring data associated with different chemical and/or physical characteristics of the effluent fluids. It is also envisaged that the analytical component or the data acquisition component 215 may instruct the high throughput apparatus to acquire samples of fluids that are flowing through, for example, the sampling flow lines 8a, 12g. This sampling of the fluids may take place at a port in, for example, the sampling line(s) 8a, 12g and may be either manual or automated. Accordingly, the analytical component 211 or the data acquisition component 215 may either output an instruction to the operator of the apparatus to take a sample or generate an operating mode to instruct an automated sampling apparatus to take a sample of the fluids.

Figure 5:
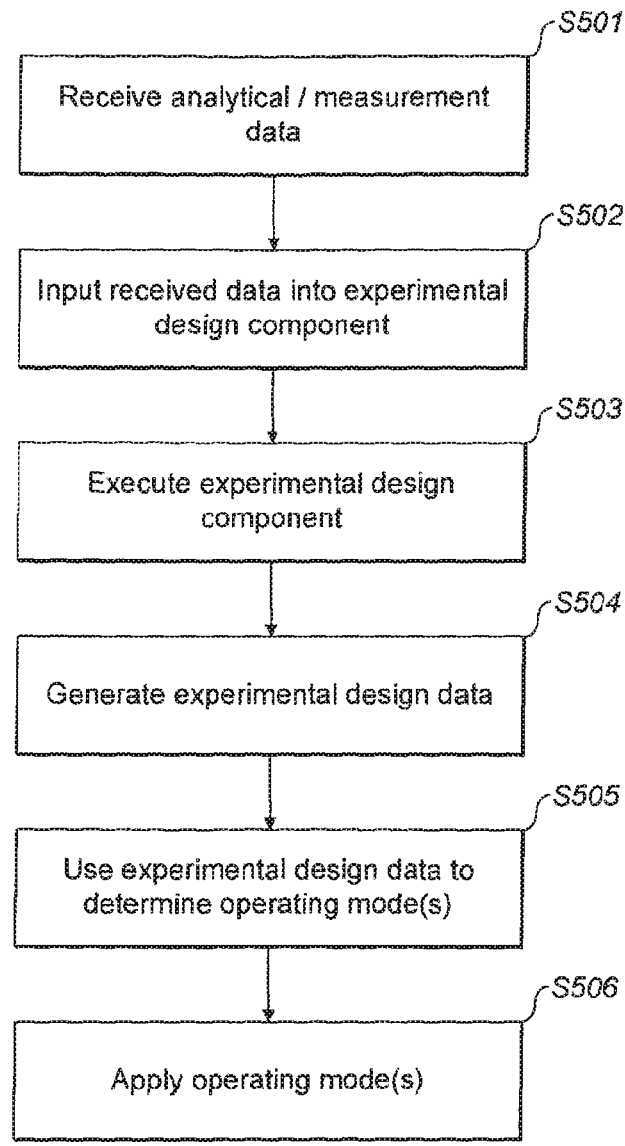
FIG. 5 shows the steps carried out in a method for determining one or more operating modes for the apparatus of FIG. 1 using an experimental design software component.
Figure 6:
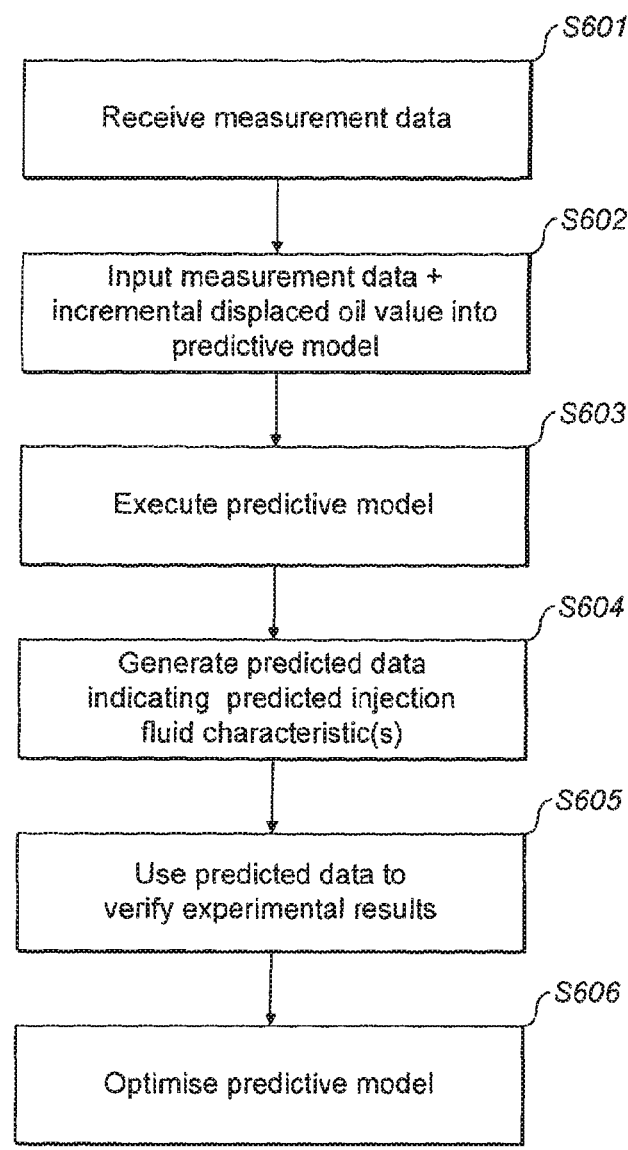
FIG. 6 shows the steps carried out in a method for determining one or more operating modes for the apparatus of FIG. 1 using a predictive model.

Referring to FIG. 5, the experimental design component 213 is configured to identify and design, from the results of the analytical component 211 algorithms and/or the measured data received (step S501, which corresponds to either step S401 or S404 of FIG. 4) by the control system 200, further experiments having optimised characteristics that result in or improve upon a required effect, such as an improvement in incremental oil recovery. Thus, the experimental design component 213 may correlate different levels of incremental oil recovery for different experiments performed using the high throughput apparatus to variable experimental parameters, such as the chemical composition of the injection fluid, oil, formation water or porous media or physical parameters of the injection fluid, oil, formation water or porous media. The experimental design component 213 may then identify potential improved and preferably optimal compositions for injection fluids. Accordingly, the received data is input at step S502 into the experimental design component 213, and at step S503, the experimental design component 213 is executed according to predetermined rules, for example in the form of various algorithms (which are preferably stored in and accessible from the storage component DB2 as necessary, and automatically executed according to the parameters of the data received), to generate (step S504) experimental design data.

The experimental design component 213 can be configured to rank the results of completed experiments with respect to incremental oil recovery and to compare these to a required effect of a future experiment, such as a desired volume of recovered oil. The experimental design component 213 is also configured to correlate the fluid release profile(s) generated by the analytical component 211 to a measurement of the incremental oil recovered from each sample 1. The experimental design component 213 may also determine correlations between different chemical and/or physical characteristics of the injection fluids, produced fluids, formation waters, oil or porous media of the completed experiments, and known incremental oil recovery results, thereby allowing appropriate algorithms of the experimental design component to devise further experiments that optimize the injection fluids for the samples of porous media. In particular, the experimental design component 213 may include statistical experimental design software that is configured to devise additional experiments based on initial output data from a primary screening.

Preferably, the experimental design component 213 uses a statistical correlation approach in order to identify the factors that influence the experimental results. Multiple regression analysis can be performed, and a respective weighting of each parameter that can contribute to the incremental oil recovery can be established. Certain parameters of those that affect incremental oil recovery will contribute to the calculated value more than others, and this can be captured via a weighting scale of 0 to 1, for which parameters that have a higher weighting are more significant than those that have a lower weighting. Multiple regression analysis minimises the effect of errors in the measurement data that arise from the experiments, and hence optimal parameter values or an optimal range of values may be calculated for use in future experiments. A bespoke experimental design software package may be employed or statistical packages such as JMP® (supplied by SAS Inc) or STATISTICA (supplied by StatSoft Ltd) may be used.

For example, the results of an initial screening (i.e. a primary set of flooding experiments) may be used to determine whether or not there is any incremental oil recovery when a certain additive is added to a particular injection fluid; to determine whether or not any oil is recovered at all, or whether an amount of oil over a predetermined threshold value is recovered. Based on technical and economical factors, it is preferable to use as little additive as possible in the injection fluid, however, the quantity of additive used may impact on the amount of incremental oil recovered. The initial screening may be performed with a relatively high concentration of additive, and based upon results generated by the analytical component 211 the experimental design component 213 may design further experiments to optimize the concentration of additive, typically by reducing the concentration of additive. The initial concentration of the additive may be 25,000 ppm, and based on the volume of incremental oil recovered by the initial screening, a determination is made by the experimental design component 213 to perform a second screening with an injection fluid having a reduced additive concentration of 10,000 ppm, and an instruction to this effect is sent to the apparatus controller 223 accordingly. If the incremental oil recovered during the second screening does not decrease beyond an acceptable predetermined amount, the additive concentration can be reduced again. The reduction can continue until the incremental oil recovered is insignificant, and an optimum value for the additive concentration can be investigated further.

Each of the analytical and experimental design software components 211, 213 is further able to determine (step S505, which corresponds to step S405) instructions comprising an operating mode on the basis of the data output thereby. The operating mode is applied at step S506 (which corresponds to step S406) by sending the operating mode to the apparatus controller 223, where the instruction is executed by control software associated with the controller 223. The apparatus controller 223 executes the operating mode to control the physical apparatus according to the generated experimental design data (e.g. to close a valve 10a, 10b, inject a fluid via a specific inlet 5, operate a pump 10c, etc.).

The experimental design component 213 may take input from or be executed in conjunction with a predictive waterflood model 217, similar to that described in International patent application number PCT/GB2010/001038. The predictive model 217 is configured to generate predictive data, for example, a theoretical prediction of the amount of incremental oil recovered when using a particular set of measurement data representative of the physical and/or chemical characteristics of the injection water, oil, porous medium, etc before any physical experimentation has taken place. Alternatively, a predetermined threshold value of a required amount of incremental displaced oil, compared with the predetermined volume of oil, is input (step S602) into the computer-implemented predictive model 217, together with the measurement data received (step S601) from measuring one or more characteristics of the rock formation, the crude oil and the formation water, and upon execution of the predictive model 217 (step S603) predictive data indicative of one or more predicted characteristics of the injection fluid is generated (step S604). For example, the generated predictive data can relate to a total dissolved solids (TDS) content and/or multivalent cation content of the displacement fluid necessary to displace at least the predetermined threshold value of incremental displaced oil that was input into the predictive model 217. Thus the characteristics of the injection fluid that is required to displace a required amount of incremental oil can be predicted.

The predictive model 217 may be used at step S605 to verify that the experiments performed by the apparatus conform to an initial prediction and, if so, the predictive model may be used to aid in the optimization of the experimental design component 213 calculations. Alternatively or additionally, the correlations resulting from the execution of the experimental design component 213 may be used by an optimization component 219 at step S606 to optimize the algorithms and constraints of the predictive model 217. For example, if the initial experiments do not conform with the initial prediction, any potential errors can be identified and investigated before further experiments are carried out, and once any problems are identified, the experiments may be repeated. However, should the same set of results be obtained upon repeating the experiments, then it will be necessary to update the predictive model 217 to take into account the additional unexpected results. As more and more measurement data is accumulated by the control system 200, the optimization component can iteratively adjust programming rules of the predictive model 217 to optimize the accuracy thereof.

The predictive model 217 may comprise a statistical software package such as that provided by SAS® JMP®. The relevant data is compiled, for example into a Microsoft® Office Excel spreadsheet, which is opened using the SAS® JMP® package. A series of crossplots of specific characteristic data against a value for the benefit gained (for example, the incremental oil percentage) are produced using the "Analyze, Fit Y by X" function, for example, a crossplot of incremental oil percentage against oil API, or incremental oil percentage against the calcium concentration of the injected water. The crossplots are then used to build a high level picture of which characteristics are most relevant (i.e. produce the best correlations). A software tool which applies principle component analysis to the data can be used to determine which characteristics to input into a "Fit Model" function. Alternatively, a choice of characteristics can be made manually. The incremental oil percentage data is then added to the "Y variables" and other chosen characteristics are added to "construct model effects". The model results are then exported to a program such as Microsoft® Office Excel and a test fit can be applied with existing data in order to verify the model.

The control system 200 preferably provides a graphical user interface (GUI) to permit users to add input for consideration in, or override the automated design by the experimental design component 213. The experimental design component 213 is able to analyze the data output from the analytical component 211 for significant statistical correlations according to a set of predetermined rules, and then the output from this algorithm is displayed visually, e.g. graphically, to alert the user to the correlations found. The GUI may be configured to receive data generated by the experimental design component 213, specifically data indicative of various experiments generated at step S503, as described above; however, the user may override this manually using a knowledge based assessment to determine the next experiments to be performed. For example, the user may be aware of factors which are not programmed into the algorithms constituting the experimental design component 213.

Measurement data received by the control system 200 are based on measured chemical and/or physical characteristics of the formation water, the oil, the test injection fluid, the sample of porous medium, and the fluid produced from the sample 1 of porous medium for each of the simultaneous experiments. The measurement data may comprise specific measured chemical or physical values as directly measured by the one or more suitably positioned analytical instruments 7, 11, or ratios of values of chemical or physical characteristics, or may comprise values derived from a number of separate chemical or physical characteristic measurements, according to known techniques. Data from earlier high throughput experiments may be stored in the storage components DB1, DB2 such that for each high throughput run (simultaneous flooding experiments), the experimental results may be compared by the experimental design component 213 with results obtained from earlier high throughput runs.

Data obtained from off-line analysis of chemical or physical characteristics of the fluids or porous media may also be stored within the storage components DB1, DB2 of the control system 200.

The experimental design component 213 can be configured to order or rank different injection fluids, for example, injection waters in priority order based on the results of the high throughput experiments. These results may alert the user to further experiments that should be undertaken using the high throughput apparatus in order to optimize an injection fluid for a particular reservoir (particular reservoir rock, formation water and oil). Alternatively, the software may alert the user to a suitable injection water for a reservoir that gives a good level of incremental oil recovery taking into account factors such as available volume of the base injection water, and cost of additives compared with the incremental oil recovery.

It may also be possible to automate the injection of test fluids for each sample 1 of porous medium. Thus, injection of the test fluid, for example, an aqueous fluid, may continue until detectors downstream of the holders 2 signal that no further oil is being produced. A flood with an aqueous fluid may be performed in secondary mode, with different injection waters being ranked by the control system 200 on the basis of the amount of oil produced from the samples 1 of porous media. Alternatively, the flood may be in tertiary mode wherein each sample 1 is initially flooded with a synthetic or naturally occurring high salinity water and the amount of oil produced determined. The core samples 1 are then flooded with different types of injection water to test for the production of any incremental oil. If incremental oil production is detected downstream of a holder 2, the automated system will continue to inject the injection water until no further incremental oil is produced.

The composition of the injection fluid may be maintained substantially constant with respect to time during testing. Alternatively, after a sample 1 of porous medium has been reduced to residual oil saturation with a particular injection water, the composition of the injection water may be changed to determine if additional incremental oil may be recovered from the sample 1 of porous medium. For example, the concentration of an additive for the injection water may be increased after the sample 1 has attained residual oil saturation to see if the increase in concentration of the additive results in further incremental oil recovery.

Additional Data

Additional data relating to chemical and/or physical characteristics of the porous media, formation water, oil and injection fluid may be determined off-line.

For example, where the samples 1 of porous media are core plug samples, the core is typically subjected to chemical analyses to determine chemical characteristics such as: the whole rock clay content of the reservoir rock, which can be determined by X-ray diffraction (XRD), scanning electron microscopy (SEM) or infrared scintillation point counting; the mineral content of the clay fraction of the rock, in particular, clays of the smectite type (such as montmorillonite), pyrophyllite type, kaolinite type, illite type, chlorite type, and glauconite type, which can be determined by X-ray diffraction (XRD) or scanning electron microscopy (SEM). Physical characteristics such as porosity and permeability may also be determined. By inputting these chemical and physical characteristics into the control system 200 software components, correlations between these characteristics and the results of the coreflooding tests can be determined.

Other preferred or more specific chemical characteristics which may be measured to provide analytical data for input into the control system 200 software components include: a whole rock XRD analysis of the rock formation, including all mineral types in reservoir rock (including clays, and transition metal compounds, such as oxides and carbonates, for example, iron oxide, siderite, and plagioclase feldspars); the zeta potential of the rock.

The oil that is to be tested using the high throughput method and apparatus of the present invention may also be analysed for chemical and physical characteristics. Chemical characteristics of the oil include the total acid number (TAN) value; the base number of the oil; the content of asphaltene and resin components of the oil; the total nitrogen content of the oil (ppm wt) and basic nitrogen content of the oil; the total sulphur content of the oil (ppm wt); the total oxygen content of the oil ppm wt; a total oil SARA analysis (SARA stands for saturates, aromatics, resins and asphaltenes and is a full evaluation of how much of each type of oil component is present in a sample 1); and the mass spectral composition as obtained for example by electrospray Fourier Transform ion cyclotron resonance mass spectroscopy. Physical characteristics of the oil include the American Petroleum Institute (API) gravity (relative density) of the oil) and the oil viscosity at reservoir temperature and pressure, the viscosity of the oil at standard conditions (for example, the viscosity measurement may be made at 20° C., 25° C. and 30° C.). Additional parameters of the oil that can be taken into account as required in order to configure the experimental design component 213, that correlates the results of the coreflood apparatus with different variables that are changed using the experimental design protocol, include: pour point temperature of the oil (° C.); cloud point temperature of the oil (° C.); density of the oil at 15° C. (g/ml) or at some other standard temperature; boiling point distribution of the oil (wt %); boiling point distribution of the oil (° C.); surface tension of the oil (mN/m); oil/salt water interfacial tension (mN/m); and oil/fresh water interfacial tension (mN/m).

Similarly, the chemical characteristics of the formation water and of any injection water may be tested using the high throughput method and apparatus of the present invention and the data input into the experimental design component 213. These chemical characteristics include the total dissolved solids content (TDS), the total multivalent cation concentration, the concentration of individual cations that are naturally occurring in formation and injection waters (such as sodium, potassium, magnesium, calcium, barium and iron), the concentration of individual anions that are naturally occurring in formation and injection waters (such as sulfate, phosphate, nitrate, nitrite), and the pH of the water. The chemical characteristics of the injection water may also include the concentration of additives such as anions (e.g. anions used for microbial enhanced oil recovery, MEOR), cations (e.g. cations used for crosslinking polymers), surfactants and polymers.

Cleaning and Ageing Procedure for the Samples of Porous Media

The samples 1 of porous media, for example, core plugs are preferably cleaned before carrying out the simultaneous flooding experiments using the high throughput apparatus of the present invention. For instance, where the samples 1 are core plugs or sandpacks formed from produced sand, they may initially contain many substances within their pores, e.g. formation water, drilling mud, crude oil. If deemed necessary, the plurality of samples 1 of porous media (each arranged within one of the holders 2) are cleaned by flushing the samples 1 with solvents (typically toluene followed by methanol) until all the oil has been flushed out of the samples 1. Where the cores contain reactive clays such as smectite clays, the cores are preferably cleaned with kerosene and isopropanol as opposed to the more usual solvents, toluene and methanol so as not to artificially change the absolute permeability of the cores through mobilization of the clays. The cleaning process is enhanced if the solvents are alternated a plurality of time.

When cleaning the samples 1 with solvents prior to performing the high throughput experiments, on-line analysis of the solvent may be used to detect differences between the solvent immediately upstream and downstream of the holders 2 (for example, to detect signals in the effluent arising from chemical impurities (for example, oil components) that have been eluted from the samples 1 of porous media). When there are no differences between the chemical characteristics of the injected solvent and the effluent solvent, the samples 1 of porous media are considered to be clean. As discussed above, it may be necessary to switch between cleaning solvents to achieve efficient cleaning of the samples 1. Cleaning of the samples 1 may be automated by using software associated with the apparatus controller 223 that controls switching between solvents, for examples, software that opens and shuts valves leading to different solvent storage vessels (e.g. reservoirs 14) thereby controlling the flow of solvents through the samples 1 of porous media. Preferably, this software terminates cleaning of an individual sample 1 of porous medium when an operating mode received from the analytical component 211 indicates that there are no chemical impurities in the solvent that is eluted from the sample 1.

Once the samples 1 have been cleaned (if necessary), they are then saturated with a brine of known composition, which brine may be intended to simulate the connate water or formation water (for example, mixture of connate water and previously injected water such as seawater or produced water) that is present in the reservoir under investigation. By connate water is meant the water originally present in the reservoir before migration of oil from a source rock into the reservoir rock.

Thus, the composition of the synthetic formation brine may vary depending upon the reservoir under investigation. When the samples 1 are fully saturated with brine they are said to be at 100% water saturation ($S_w$=1). Typically, the samples 1 of porous media may be brought to 100% water saturation by forcing the brine through the samples 1 under vacuum (for example, using a suction filter assembly). This suction filter assembly may be separate to the high throughput apparatus in which case the holders 2 are removed from the apparatus so that the samples of porous media may be placed in the suction filter assembly. Alternatively, the holders 2 may be retained in the high throughput apparatus, in which case a valve located on each effluent line 8 may be opened to connect the holders 2 and their associated samples 1 to a vacuum line and a synthetic formation brine may be fed to the inlets 5 of the holders 2. It is also envisaged that the brine may simply be injected through the samples 1 (with the holders 2 retained in the high throughput apparatus) for a sufficient period of time to ensure 100% water saturation.

The next step involves a primary drainage of the cores to an irreducible brine saturation, $S_{wi}$, (also referred to as initial water saturation). This drainage may be carried out by injecting and driving a non-wetting phase or an oil through the samples 1 of porous media which are initially 100% saturated with brine.

The step of restoring the samples 1 to irreducible or initial water saturation ($S_{wi}$) may be achieved using a confined porous plate technique. Typically, the samples 1 of the porous media are each arranged on porous plates that have a permeability at least one to two orders of magnitude lower than that of the samples 1. It is important that there is good contact between the porous plate and the sample 1, typically, this may be assured by inserting filter paper (which may comprise a wicking medium such as fibre-glass) between the porous plate and the sample 1. This also helps to ensure that the porous medium is in contact with a water wetted surface. Each sample 1 is typically arranged substantially vertically on the porous plate, with the longitudinal axis through the cylindrical sample aligned with the vertical axis. Once the sample 1 is installed on the porous plate, a non-wetting phase such as air, nitrogen, or a mineral oil, or an oil such as an organic oil, crude oil or a distillative fraction thereof such as kerosene (hereinafter "oil phase"), is injected into the sample 1 at a constant pressure to displace a portion of the connate brine (or formation water) from the sample and through the porous plate thereby providing a desired aqueous phase to non-wetting phase or oil phase ratio. Owing to the non-wetting phase or oil phase being injected at a constant pressure and the large difference in permeability between the samples 1 and the porous plates and the plate being completely water wet, the injected non-wetting phase or oil phase is unable to flow out of the samples 1 of porous media. When the samples 1 are saturated with non-wetting phase or oil phase at the irreducible water saturation, water is no longer being produced from the samples 1, and the cores are defined as being at $S_{wi}$. If the oil phase is crude oil, the samples 1 are now saturated with crude oil at $S_{wi}$. If a non-wetting phase is employed or the oil phase is an oil other than crude oil, the non-wetting phase or oil phase from the samples 1 is displaced using crude oil by injecting crude oil into the samples 1 at a constant pressure leaving only water and crude oil occupying the pore space of the samples 1. The samples 1 are now saturated with crude oil at $S_{wi}$ and are at initial oil saturation ($S_{oi}$).

If $S_{wi}$ is acquired by injecting and driving kerosene through the samples of porous media (which are initially 100% saturated with brine), the kerosene is typically displaced by a buffer of toluene before displacing the toluene with oil. The buffer of toluene is used to prevent deposition of asphaltenes from the crude oil which can otherwise occur if crude oil contacts kerosene.

If $S_{wi}$ is acquired by injecting a gas (for example, an inert gas such as nitrogen), through the samples of porous media (which are initially 100% saturated with connate brine or formation water), the gas is then typically displaced with crude oil (under a back-pressure) to achieve initial oil saturation ($S_{oi}$). However, an oil (other than crude oil) may be used to displace the gas (for example, kerosene), and this oil is subsequently displaced with crude oil.

$S_{wi}$ is typically acquired using a non-wetting phase or oil phase (other than crude oil), where the crude oil is viscous and therefore does not readily displace the formation water from the pore space of the samples of porous media.

Where core plugs are being employed, the crude oil is typically taken from the reservoir from which the core samples 1 were obtained.

The crude oil may be either a "dead" oil or a "live" oil that has been recombined with gas. Where the crude oil is a "live" oil, the gas remains in solution owing to the elevated pressure maintained in the apparatus and cores.

If desired, driving the samples 1 to initial or irreducible water saturation may be performed using a separate porous plate apparatus. The samples 1 at initial water saturation $S_{wi}$ are then loaded into the holders 2. However, it is also envisaged that the high throughput apparatus may initially be set up such that the samples 1 of porous media are arranged in holders 2 having end porous plates instead of end patens 3, 4. After cleaning the samples 1 and bringing the samples to $S_{wi}$, the porous plates are then replaced with platens 3, 4 for the high throughput flooding tests.

It is also possible to bring the samples 1 of porous media to $S_{wi}$ using centrifugal techniques. Thus, a plurality of samples 1 of the porous media that are 100% saturated with water ($S_w=1$) are placed in a plurality of centrifuge tubes. Oil is then added to the tubes before placing the tubes in a centrifuge. After centrifugation, the samples 1 of porous media will be at $S_{wi}$ and the tubes will contain both oil and water. Alternatively, Swi may be achieved by centrifuging the samples 1 under a blanket of a non-wetting gas in which case it is then necessary to displace the non-wetting phase with crude oil (optionally via an intermediate oil). This technique is suitable for samples 1 of core and for small sandpacks (where the sandpacks are contained within a sleeve having flits at each end to allow oil to displace a portion of the water from the pore space of the sandpack). The samples 1 of porous media at initial oil saturation ($S_{oi}$) are then loaded into the holders 2 of the high throughput apparatus.

The initial oil phase saturation level ($S_{oi}$) may be selected to replicate the conditions likely to be found within a reservoir, for example, by changing the pressure of the oil that is injected into the samples 1 for the porous plate technique or by changing the spin speed of the centrifuge. For instance, oil may be added to the samples 1 in the required amount to give an initial oil saturation level of from 0.4 to 0.9, for example, 0.5 to 0.7.

In the laboratory, it may be possible to control conditions using the software components of the control system 200 described above such that the sum of the initial oil saturation level ($S_{oi}$) and the initial water saturation ($S_{wi}$) equals unity, i.e. $S_{oi}+S_{wi}=1$. This means that the pores of the porous media are completely full and only contain oil and water. In general, however, it is more probable that $S_{oi}+S_{wi}$ will be slightly less than unity, since other phases such as air may be present in small amounts within the pores. However, for the purposes of the high throughput experiments, the sum of $S_{oi}$ and $S_{wi}$ is assumed to equal unity.

A nominal overburden pressure of 350 to 5000 psi, for example, about 400 psi, is then applied to the samples 1 of porous media that are at $S_{wi}$. Thus, each sample 1 of porous medium that is loaded into each holder 2 is provided with a rubber sleeve that is open at each end. O-rings at the first and second ends of the sample form a fluid tight seal with the holder 2. A fluid is injected under pressure into the annulus formed between the rubber sleeve and the inner wall of the holder 2 such that an overburden pressure of about 400 psi is applied to the rubber sleeve and hence to the side wall of the sample of porous medium. This is the containment pressure for the samples 1 of porous media. The fluid that is injected into the annulus may be water, a hydraulic oil or a gas, typically an inert gas such as nitrogen.

Ageing of Samples of Porous Media

The plurality of samples 1 of porous media (for example, core plug samples) at initial water saturation ($S_{wi}$) and initial oil saturation ($S_{oi}$) are then aged (left to equilibrate) at the desired experimental temperature e.g. reservoir temperature and desired experimental pressure. The ageing process is applied for a period of time sufficient to restore the samples 1 to the wettability conditions typically encountered in the reservoir. During the ageing process, the oil is optionally periodically replaced by "fresh" oil, for example, a 1 to 2 pore volume of oil may be refreshed weekly during the ageing process.

During this ageing process, a proportion of the water that is initially in contact with the surface of the pores of the porous media (for example, surface of the rock) is replaced with the oil over time, which gives a more realistic representation of the wettability of the porous media (for example, rock) for subsequent steps in the experiment.

For instance, it will be appreciated that when the samples 1 are 100% saturated with aqueous phase (i.e. before any oil is added), the aqueous phase will occupy the entire pore volume of the samples. Considering a single pore, when oil is initially present in the sample 1 at $S_{wi}$, the oil will generally have displaced the aqueous phase from the bulk region of the pore such that the water remains in contact with the pore surfaces. During ageing the oil and water will redistribute within the pore, e.g. such that a portion of the pore surface is contacted by the oil. Accordingly, after aging, the pore will be in a mixed wettability state.

Wettability controls the fluid distribution in a reservoir and therefore exerts a fundamental influence on flow behaviour, residual oil saturation and relative permeability. Accordingly, wettability also has a fundamental influence on reservoir performance. The inventors in the present case have recognized that, it is most desirable that the wettability distribution within each sample 1 of porous medium is representative of a reservoir. They have further recognized that the ageing process should be allowed to run its course before the samples 1 are used in any subsequent flooding experiments. If ageing is not complete or is not substantially complete, then any predictions based on the results of such subsequent experiments may be prone to a higher degree of error, since the samples will not closely replicate reservoir conditions.

Complete or sufficient ageing of the samples 1 may take a prolonged period of time, for instance sometimes of the order of several weeks or even months, in particular three to six weeks.

Ageing of the samples 1 of porous media may be monitored using NMR spectroscopy, as described in copending UK patent application number GB 1007694.1, in which case the holders 2 for the samples 1 should be formed from a plastics material. Thus, the holders 2 containing the samples of porous media, are periodically shut-in and removed from the high throughput apparatus for off-line NMR analysis.

Thus, in the case of flooding experiments, the fluids that are contained in the pore space of the samples of porous media prior to injection of the injection fluid are oil and formation water.

Determination of Pore Volumes to Oil and Water

Preferably, as part of the preparation protocol, additional tests may be carried out on each of the samples 1 of porous media to determine the accessible pore volume to water of each sample 1 at $S_w=1$ and the accessible pore volume to oil at $S_{wi}$. This allows the incremental oil recovery (in pore volumes) to be determined with respect to the injected volume of water (and converted into pore volumes of oil). Thus, the volume of oil produced (ml) may be divided by the oil pore volume and the volume of water injected (ml) is also divided by the oil pore volume. This allows the incremental oil production for the simultaneous flooding experiments to be directly compared.

The accessible pore volume to water at $S_w=1$ may be obtained by injecting a brine comprising a tracer, typically, iodide or lithium. The effluent removed from each sample 1 is then analyzed for iodide or lithium concentration, for example, using an inductively coupled plasma detector (ICP) or a density meter, and the concentration profile ($C/C_0$) for the volume of brine injected is used to provide an estimate of the accessible pore volume of the sample 1 to water (wherein C is the concentration of tracer in the effluent and $C_0$ is the concentration of tracer in the injection brine). A second measurement may be obtained by measuring the decline in tracer concentration in the effluent when the injection fluid is switched to a brine containing no tracer. Thus, the pore volume is the volume of brine injected when $C/C_0$ is 0.5. The total pore volume may be approximated as the sum of the water pore volume and oil pore volume. Accordingly, the oil pore volume=1−water pore volume.

Alternatively, the accessible pore volume to oil at $S_{wi}$ may be directly determined for each of the samples 1 of porous media by injecting oil containing a tracer (typically iodododecane or iododecane) into the cores. The effluent is analyzed for concentration of the tracer (C) and the concentration profile ($C/C_0$) for the volume of oil injected is used to provide an estimate of the accessible pore volume to oil at $S_{wi}$, in a similar manner for determining the accessible pore volume to water (wherein $C_0$ is the concentration of tracer in the injected oil). A second measurement can be obtained by measuring the decline in tracer concentration of the effluent when the injection fluid is switched to oil containing no tracer.

Simultaneous Flooding Experiments

Simultaneous flooding experiments may be performed in tertiary mode for each of the samples 1 by injecting into each sample 1 an injection fluid, for example, brine of known composition (for example, a synthetic seawater or a synthetic low salinity water) at constant flow rate until no oil is being produced from the core. The core is now at a first residual oil saturation, $S_{or1}$. The effluent produced from each core may be sampled for off-line analysis or may be analyzed using the one or more on-line analytical instruments 7, 11. The volume of produced oil is also determined. These are the control floods for comparison with subsequent coreflooding with various test injection fluids, for example, various injection waters (tertiary mode flooding).

At this point, the brine may be switched to a brine of similar composition that has been doped with a dopant such as iodide or lithium. For example, a portion of the chloride ions in the original brine may be replaced with iodide ions or a portion of the sodium ions in the original brine may be replaced with lithium ions. The accessible pore volume to water of the sample 1 of porous medium following this initial waterflood (secondary recovery) is then determined, as described above. Owing to the brine having a similar composition to that of the brine used during secondary recovery, no incremental oil recovery will be observed during this test. The residual oil saturation after this control flood, $S_{or1}$, may be determined from the water pore volume following this initial water flood (i.e. $S_{or1}=(1-$water pore volume following secondary recovery)). The amount of oil produced in this initial waterflood together with the value for the initial oil saturation ($S_{oi}$) can also be used to determine a value for $S_{or1}$. Thus, $S_{or1}=(S_{oi}-$pore volume of oil produced during secondary recovery).

Test injection fluids having different compositions to the initial brine are then injected into the samples 1 for a sufficient period of time to determine whether any incremental oil recovery is observed. If oil is produced from one or more of the samples 1, injection of the test injection fluid will continue until production of oil ceases. The amount of incremental oil produced is then determined. At this stage, the accessible pore volume of the core to water may also be determined, as described above, by using a brine of similar composition to that of the test aqueous injection fluid.

If there has been no incremental oil recovery with the test injection fluid, $S_{or2}$ will be the same as $S_{or1}$.

If there has been incremental oil recovery, a value for $S_{or2}$ is determined from either the pore volume of water after the tertiary recovery with the test injection fluid or from the amount of incremental oil produced during tertiary recovery. Thus $S_{or2}=(1-$water pore volume following tertiary recovery) or $S_{or2}=(S_{oi}-$total pore volume of oil produced during secondary and tertiary recovery) or $S_{or2}=(S_{or1}-$pore volume of oil produced during tertiary recovery).

The additional or incremental amount of oil that is obtained when different injection waters are injected into different samples 1 of porous media in tertiary recovery mode is an amount in terms of, for example, a percentage, fraction or volume, of oil that will be displaced or recovered compared with a predetermined volume of oil for a "base" oil displacement (or recovery) volume, for a base waterflood using a base injection water such as a synthetic high salinity fluid. This base value is the amount of oil recovered in the effluent from the cores at standard physical conditions such as injection pressure, volume of base injection fluid employed, and injection rate). Typically, the additional or incremental amount of oil is expressed as a percentage or fraction of the predetermined base value.

Alternatively, the samples 1 may be tested in secondary mode, by omitting the step of waterflooding the samples with the synthetic brine to $S_{or1}$. Instead, the samples are directly flooded with the test injection fluid, for example, test injection water. This will allow a coarse screening of the test injection fluids by determining whether oil is produced from the cores or not.

Typically, the injection fluid employed for each of the simultaneous coreflood experiments (e.g. an injection water) is injected into each core at a flow rate in the range of 1 to 40 ml/hour, preferably 4 to 10 ml/hour, for example, 3 to 5 ml/hour, preferably about 4 ml/hour so as to correspond to typical reservoir frontal advance rates. Reservoir frontal advance rates are dependent upon the rate at which the injection fluid is injected into the injection well and the area into which the fluid is injected (radius from the injection well and the reservoir interval across which the fluid is injected). A typical frontal advance rate is about 1 foot per day. All recovery varies with injection rate. Accordingly, for comparative purposes the injection rates for the plurality of experiments should be the same.

Typically, after the simultaneous coreflood experiments have been completed, the sample 1 of porous media, for example, core samples 1 are either discarded or reused by returning to the cleaning protocol. As will be understood by the skilled reader in the context of the present disclosure, the duration of the core flood experiments described is typically on the order of days or tens of days so precise simultaneity is not required. Therefore, as used herein the term simultaneous is generally used to mean that tests are carried out concurrently or in parallel, e.g that the "simultaneous" tests are in progress at the same time, even though they may start and finish at different times.

Determination of Relative Permeabilities of the Samples of Porous Media to Oil and Water In addition to determining incremental oil recovery for different EOR techniques, the apparatus of the present invention enables the simultaneous measurement of data required for determining the relative permeability of a plurality of samples 1 of porous media to oil and water. These measurements may be carried out as part of the simultaneous flooding experiments.

Thus, the high throughput apparatus may also be used to obtain relative permeability data for the samples 1 of porous media, in particular, for core plugs, this data being indicative of the relative ease with which the oil and water can move through the reservoir formation rock, after accounting for viscosity, absolute permeability and pressure gradient within the reservoir.

At the start of each coreflooding experiment, at $S_{wi}$, the relative permeability of water is zero (the water is immobile) while the relative permeability of oil is at its maximum. At the end of each coreflooding experiment, at Sc the relative permeability of oil is zero (no more oil can be mobilised) and the relative permeability of water is at its maximum.

Methods for determining the relative permeabilities of a core to oil and water are well known to the person skilled in the art. These methods include both steady state and unsteady state techniques. Such methods require measurement of the oil saturation profile (also referred to as the oil recovery profile over time) for the core and also the following "static" parameters: the fluid viscosities of the oil and formation water, the porosity of the core rock and its total (absolute) pore volume, the absolute permeability of the core rock to either 100% oil or 100%/o water flowing through the core, the injection pressure, the differential pressure across the core, the temperature of the core, and the flow rate through the core. Measurements of these "static parameters" are therefore taken.

Conventional online measurement equipment, for example, gamma-ray attenuation monitoring equipment (GASM) for determining oil saturation of the cores is unfeasible for the high throughput apparatus owing to the need for a plurality of gamma-ray sources and the size of the GASM equipment.

Instead, the oil saturation profile may be determined by monitoring the amount of oil being produced from the core is over time. This amount of oil is converted into oil pore volumes thereby providing the oil saturation of the core (Si-oil production in pore volumes) over time.

In addition, throughout the parallel coreflood experiments, differential pressure measurements may be taken over time. These measurements can be input into the analytical component 211 to allow a determination of the relative permeability curves (where the analytical component 211 includes the previously described additional "static" properties that are required to determine the relative permeability curves).

Accordingly, one or more pressure sensors may be arranged with respect to each core sample 1 to measure the absolute pressure of fluid input into and output from each of the cores, these or additional sensors being further arranged to measure a differential pressure across the length of each core. Temperature sensors may also be provided to measure and monitor core and flow line temperatures. Pumps arranged to inject fluid into the injection flow lines 12 may be controlled such that the flow rate of injected fluid and an injection fluid pressure are known.

Typically, the absolute permeabilities of the core samples 1 ($K_{w\ abs}$) and the absolute pore volume of the samples 1 are determined after the core samples 1 have been cleaned.

The invention claimed is:

1. An apparatus for performing coreflood experiments on a plurality of samples of porous media, comprising:
   a plurality of holders for the samples of porous media, each holder comprising a sleeve and first and second platens, the first platen having an inlet for an injection fluid and the second platen having an outlet for a produced fluid, and the samples of porous media being arranged, in use, in each of the holders such that the first platen and second platen of each holder contact a first and second end of the sample of porous medium respectively,
   the inlet of each first platen being in fluid communication with an injection line for injecting fluid into the sample of porous medium arranged in the holder,
   the outlet of each second platen being in fluid communication with a dedicated effluent line for removing fluid produced from the sample of porous medium arranged in the holder,
   an analyzer for analyzing the fluids removed from each of the samples of porous media; wherein the analyzer generates measurement data comprising the cumulative amount of oil produced over time from each of the samples of porous media and/or the quantity of oil in the fluids removed from each of the samples of porous media.

2. The apparatus of claim 1 comprising an analyzer that determines the composition of fluids removed from each of the samples of porous media over time.

3. The apparatus of claim 1 comprising an analyzer that determines the composition of fluids injected into each of the samples of porous media over time.

4. The apparatus of claim 1 further comprising a control system coupled to receive measurement data from the analyzer and configured to control the injection of fluid based on the measurement data,
   said apparatus being capable of simultaneously injecting fluids into the plurality of samples of porous media.

5. The apparatus of claim 4 wherein the injections commence in a staggered fashion with an onset delay between injections.

6. The apparatus of claim 4 comprising a fluid supply operable to control the supply of fluid for injection into the samples of porous media, wherein the control system is configured to control the fluid supply to at least one of said plurality of samples of a porous medium based on the measurement data.

7. The apparatus of claim 4 in which the measurement data is based on the quantity of oil in the fluid removed from the sample of porous medium arranged in the holder.

8. The apparatus of claim 7 in which the controller is configured to stop the injection of fluid into one of said plurality of samples in the event that the quantity of oil in the fluid removed from the one of said samples is less than a selected threshold level.

9. The apparatus of claim 8 in which the selected threshold level is one of: a selected concentration; a selected percentage by volume; and a selected percentage by mass of the fluid.

10. The apparatus of claim 4 wherein the control system is configured to control the injection of fluid into one of said plurality of samples of porous media based on measurement data associated with another one of said plurality of samples of porous media.

* * * * *